(12) United States Patent
Hirota

(10) Patent No.: US 7,738,941 B2
(45) Date of Patent: Jun. 15, 2010

(54) IMAGE DIAGNOSTIC SYSTEM AND PROCESSING METHOD THEREFOR

(75) Inventor: Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 502 days.

(21) Appl. No.: 11/730,057

(22) Filed: Mar. 29, 2007

(65) Prior Publication Data

US 2007/0232891 A1    Oct. 4, 2007

(30) Foreign Application Priority Data

Mar. 30, 2006   (JP)   .............................. 2006-096038

(51) Int. Cl.
*A61B 5/05*   (2006.01)
(52) U.S. Cl. ...................... 600/407; 600/437; 600/462; 600/473
(58) Field of Classification Search ................. 600/407, 600/437, 462, 473
See application file for complete search history.

(56) References Cited

U.S. PATENT DOCUMENTS 4,271,842 A * 6/1981 Specht et al. ............... 600/443

| 5,222,499 | A | * | 6/1993 | Allen et al. | 600/426 |
| 5,321,501 | A | * | 6/1994 | Swanson et al. | 356/479 |
| 5,615,679 | A | * | 4/1997 | Ri et al. | 600/437 |
| 6,283,917 | B1 | * | 9/2001 | Jago et al. | 600/437 |

FOREIGN PATENT DOCUMENTS

| JP | 6-343637 A | 12/1994 |
| JP | 2001-079007 A | 3/2001 |
| JP | 2001-79007 A | 3/2001 |

* cited by examiner

*Primary Examiner*—Long V Le
*Assistant Examiner*—Nigel Fontenot
(74) *Attorney, Agent, or Firm*—Buchanan Ingersoll & Rooney PC

(57) ABSTRACT

An image diagnostic system controls a probe to perform radial scanning within a body cavity, to acquire reflected signals through the probe and to produce data based on the signals. The system includes plural storage units for storing the data in line units, respectively, a writing control unit for controlling writing processing in accordance with a transmission/reception timing of the signals, and a reading control unit for controlling reading processing in accordance with rotation angles of the probe. The writing control unit writes data in the storage unit, other than the storage unit being subjected to reading processing, storing the oldest data. The reading control unit reads the data from the storage unit, other than the storage unit being subjected to writing processing, storing the latest data. The tomographic image is constructed based on the data read by the reading control unit.

16 Claims, 31 Drawing Sheets

FIG. 7
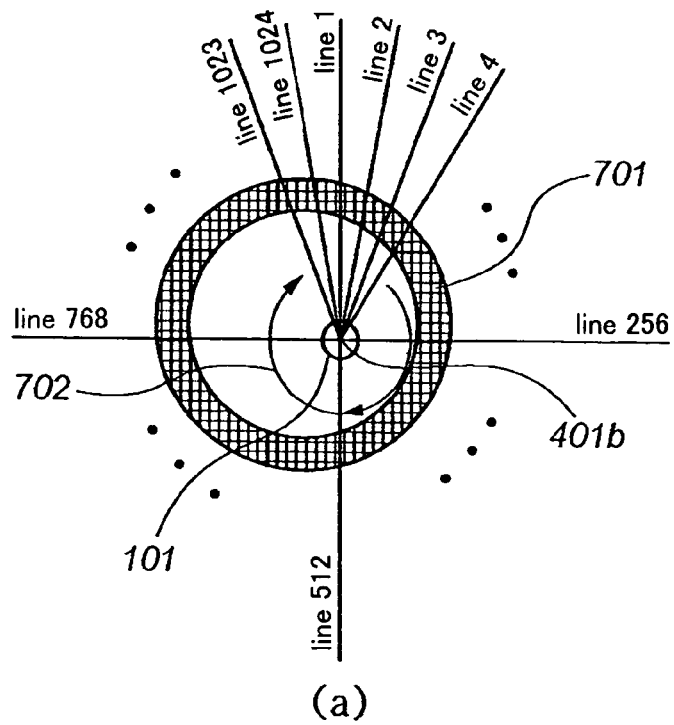
(a)
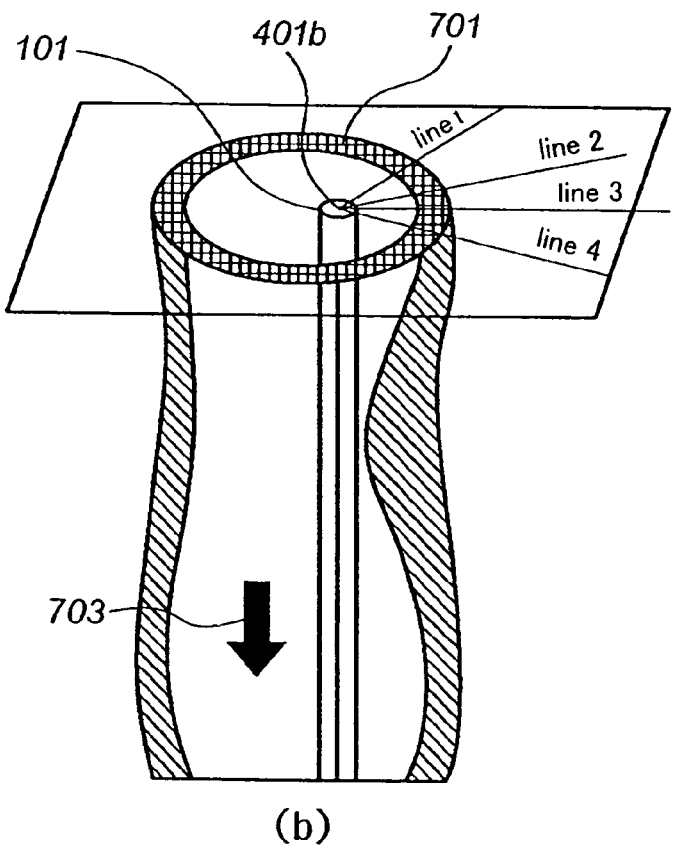
(b)

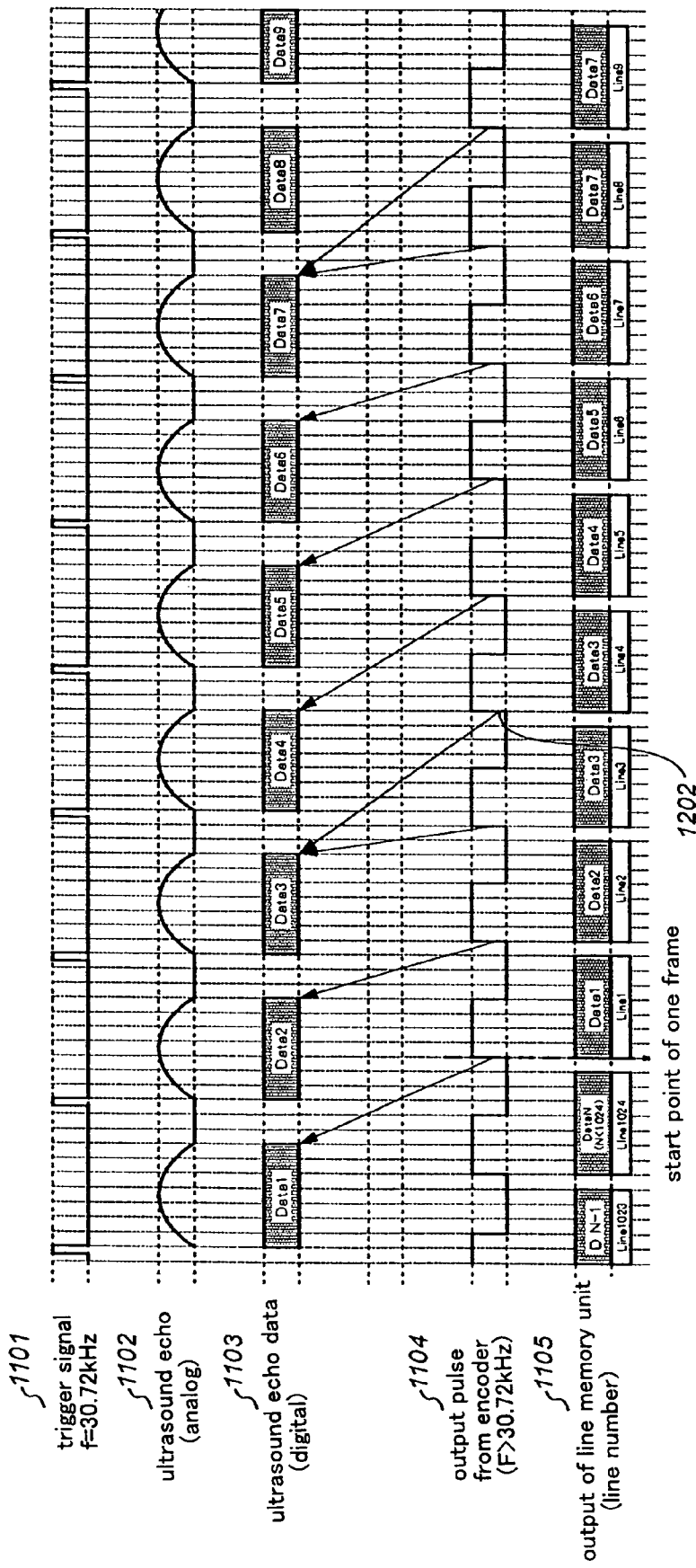

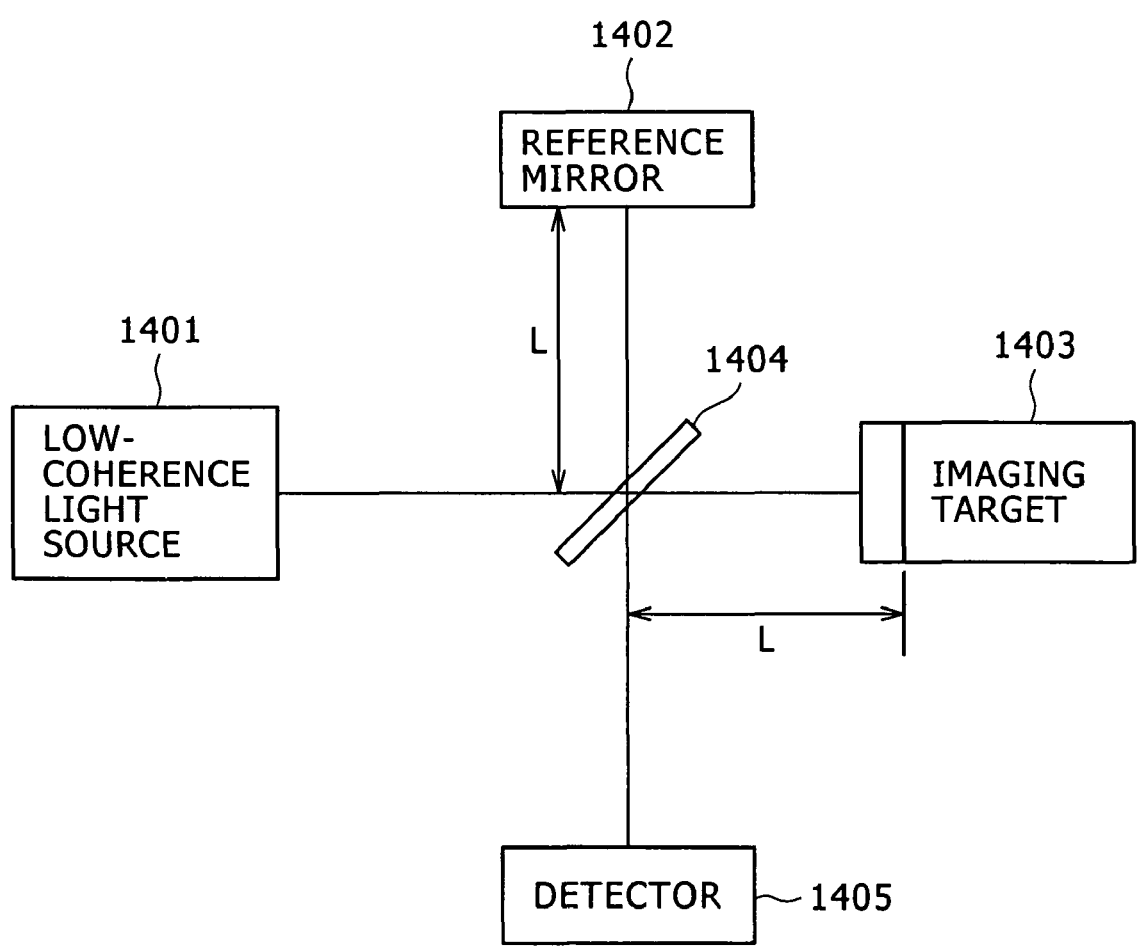

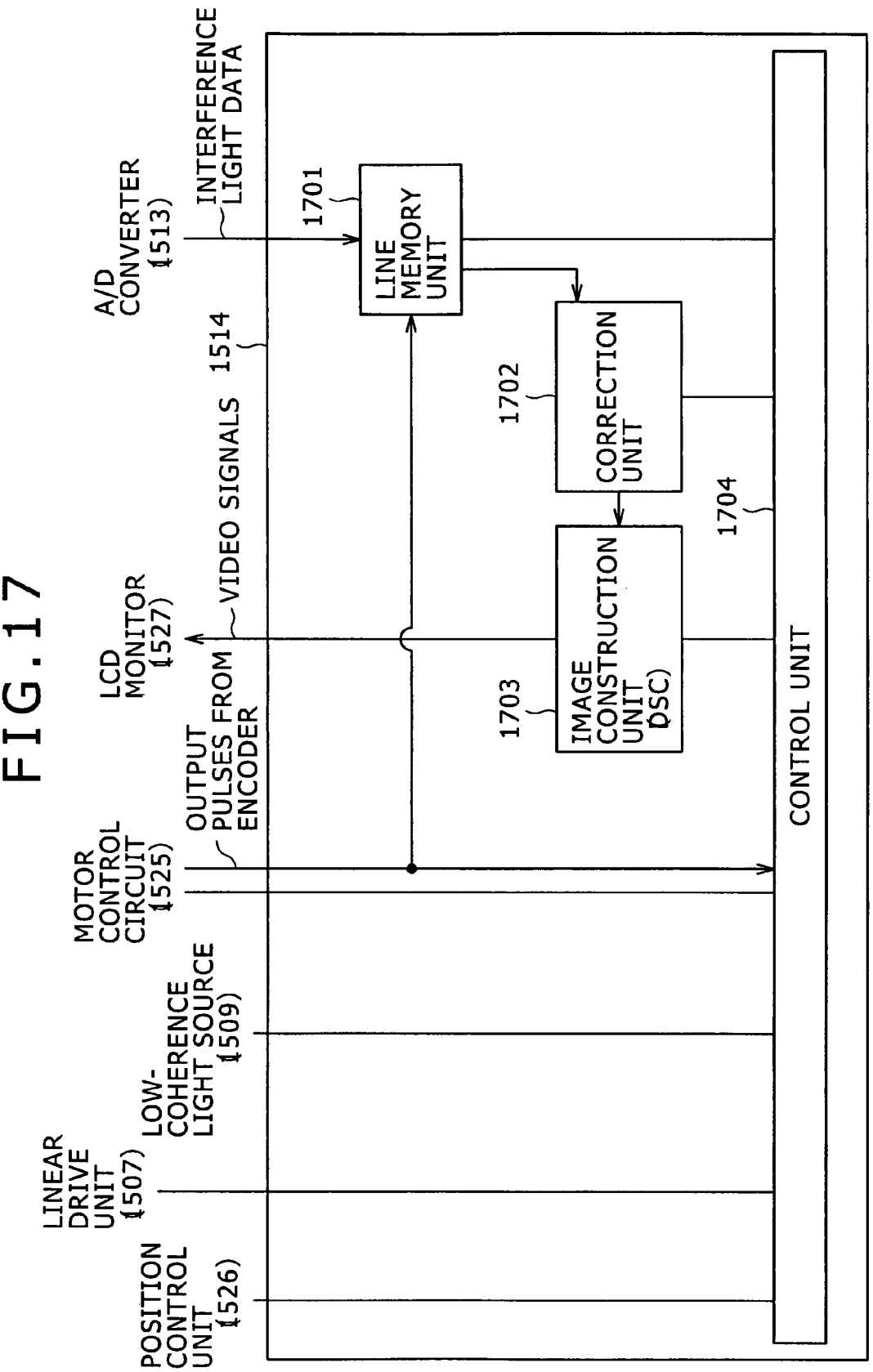

IMAGE DIAGNOSTIC SYSTEM AND PROCESSING METHOD THEREFOR

FIELD OF THE INVENTION

This invention generally relates to an image diagnostic system and a processing method for such a system.

BACKGROUND DISCUSSION

Image diagnostic systems have been used for diagnosing arteriosclerosis, for preoperative diagnosis upon coronary intervention by a high-performance catheter such as a dilatation catheter (i.e., balloon catheter) or stent, and for assessing postoperative results.

Examples of these image diagnostic systems include intravascular ultrasound (IVUS) imaging systems. In general, the intravascular ultrasound imaging system is constructed to control an ultrasonic transducer to perform radial scanning within a blood vessel, to receive a reflected wave(s) (ultrasound echoes) reflected by biotissue (e.g. the blood vessel wall) by the same ultrasonic transducer, to subject the reflected waves to processing such as amplification and detection, and then to construct and display a tomographic image of the blood vessel on the basis of the intensities of the received ultrasound echoes. An example of such a system is described in JP-A-H06-343637.

In addition to these intravascular ultrasound imaging systems, optical coherence tomography (OCT) imaging systems have been developed in recent years for use as image diagnostic systems. In an OCT imaging system, a catheter with an optical fiber incorporated therein is inserted into a blood vessel. The distal end of the optical fiber is provided with an optical lens and an optical mirror. Light is emitted in the blood vessel while radially scanning the optical mirror arranged on the side of the distal end of the optical fiber, and based on light reflected from biotissue forming the blood vessel, a tomographic image of the blood vessel is then constructed and displayed. An example of this system is described in JP-A-2001-79007.

Improved OCT imaging systems have been proposed in recent years which make use of a wavelength swept light source.

As mentioned above, there are a variety of different image diagnostic systems which use different detection principles. Nonetheless, they are all generally characterized in that a tomographic image (i.e. cross-sectional image) is constructed and displayed by performing radial scanning with a probe. For the construction and display of a high-accuracy tomographic image, it is desirable that a transmission/reception cycle of signals from the probe and a rotation cycle for the radical scanning are in complete synchronization. In general, the rotational speed of a radial scan motor is controlled in synchronization with the transmission/reception repeated at a constant clock in the probe.

The rotational speed of a radial scan motor, however, fluctuates due to variations in torque which occur as a result of changes in the degree of bending of a catheter. Therefore, it is difficult to achieve complete synchronization between the rotational speed of the radial scan motor and the cycle of transmission/reception of signals at the probe.

When a tomographic image is constructed with 1,024 lines by controlling the rotational speed of a radial scan motor, for example at 1,800 rpm (30 Hz), the transmissions/receptions can be performed in accordance with a clock speed of 30.72 kHz. If the rotational speed of the radial scan motor fluctuates by 0.05%, however the number of transmissions/receptions increases or decreases by one transmission/reception in every rotation for radial scanning.

When the number of transmissions/receptions increases or decreases by one transmission/reception in every rotation for radial scanning, the resulting displayed tomographic image is blurred in a circumferential direction or is displayed while slowly turning.

SUMMARY

According to one aspect, an image diagnostic system comprises a probe positionable in a body cavity and configured to repeatedly transmit signals into a body cavity and receive reflected signals which are reflected by biotissue surrounding the body cavity, and a control unit configured to produce data based on the reflected signals to construct a tomographic image of the body cavity and surrounding biotissue. The control unit comprises plural storage units in which are to be stored the data in transmission/reception units, a writing control unit configured to control writing processing of the data in which the data is written in the storage units in accordance with a transmission/reception timing of the signals, and a reading control unit configured to control reading processing of the data stored in the storage units in which the data stored in the storage units is read in accordance with a rotation angle of the probe. The writing control unit controls the writing processing to write the data in the storage unit in which stored data is oldest, and the reading control unit controls the reading processing to read the data in the storage unit in which the stored data is newest. A display unit is configured to display the tomographic image constructed by the control unit based on the data read by the reading control unit.

Another aspect involves an image diagnostic apparatus for controlling a probe, which is adapted to be connected to the image diagnostic apparatus and which repeatedly transmits signals into a body cavity which are reflected by biotissue surrounding the body cavity to perform radial scanning within the body cavity. The image diagnostic apparatus comprises a control unit configured to produce data based on the reflected signals and to construct a tomographic image of the body cavity and the biotissue surrounding the body cavity on a basis of the data, and a display unit configured to display the tomographic image. The control unit comprises plural storage units in which are to be stored the data in transmission/reception units, a writing control unit configured to control writing processing of the data in the storage units in accordance with a transmission/reception timing of the signals, and a reading control unit configured to control reading processing of the data stored in the storage units in accordance with a rotation angle of the probe. The writing control unit controls the writing processing to write the data in the storage unit which contains stored data that is oldest and which is not being subjected to reading processing, and the reading control unit controls the reading processing to read the data in the storage units which contains the stored data that is newest and which is not being subjected to writing processing. The tomographic image is constructed based on the data read by the reading control unit.

A method for processing information in an image diagnostic system connected to a probe comprises transmitting signals from the probe into a body cavity and receiving signals reflected from biotissue surrounding the body cavity, producing data based on the received reflected signals, performing writing processing of the data to store the data, in transmission/reception units of the signals, in individual storage units in accordance with a transmission/reception timing of the signals, and performing reading processing of the data stored in the storage units to read the data in the storage units in accordance with a rotation angle of the probe. The writing processing is performed to write the data to the storage unit which is not being subjected to reading processing and which has stored therein the data that is oldest, and the reading processing is performed to read the data from the storage unit which is not being subjected to writing processing and which has stored therein the data that is newest. A tomographic image of the body cavity and surrounding biotissue is constructed based on the data that is read during reading processing, and the tomographic image of the body cavity and surrounding biotissue is displayed.

In accordance with another aspect, a method for producing a tomographic image of a body cavity and surrounding biotissue comprises positioning a probe in a body cavity, transmitting signals from the probe into the body cavity and receiving signals reflected from the biotissue surrounding the body cavity, producing data based on the received reflected signals, writing the data, in transmission/reception units of the signals, in individual storage units in accordance with a transmission/reception timing of the signals to store the data in the storage units, with the data being written in the storage unit in which is stored the data that is oldest, and reading the data stored in the storage units in accordance with a rotation angle of the probe, with the data being read from the storage unit in which is stored the data that is newest and to which data is not being written. The method also involves constructing a tomographic image of the body cavity and the surrounding biotissue based on the data that is read, and displaying the tomographic image of the body cavity and the surrounding biotissue.

In other aspects, there are also provided a recording medium with a control program stored therein for performing by a computer the information processing method, and the control program.

The apparatus, system and method disclosed here permit production of a good quality tomographic image, even when synchronization is not achieved between the rotation cycle of a probe in radial scanning and the cycle of transmission/reception of signals at the probe.

BRIEF DESCRIPTION OF THE DRAWING FIGURES

The foregoing and additional aspects of the disclosed system and method will become more apparent from the following detailed description considered with reference to the accompanying drawing figures briefly described below.

FIGS. 7A and 7B are perspective views in cross-section of a blood vessel and the catheter section inserted therein, illustrating movements of the catheter section during an intravascular ultrasound diagnosis.

FIG. 12B is a timing chart illustrating when output pulses from the encoder and a transmission/reception timing of an ultrasonic transducer are also out of synchronization.

FIG. 14 is a block diagram schematically illustrating the basic principle of the OCT imaging system.

FIG. 17 is a block diagram schematically illustrating aspects of a signal processing unit in the OCT imaging system.

DETAILED DESCRIPTION

First Embodiment

1. General Overall Construction of IVUS Imaging System

Figure 1:
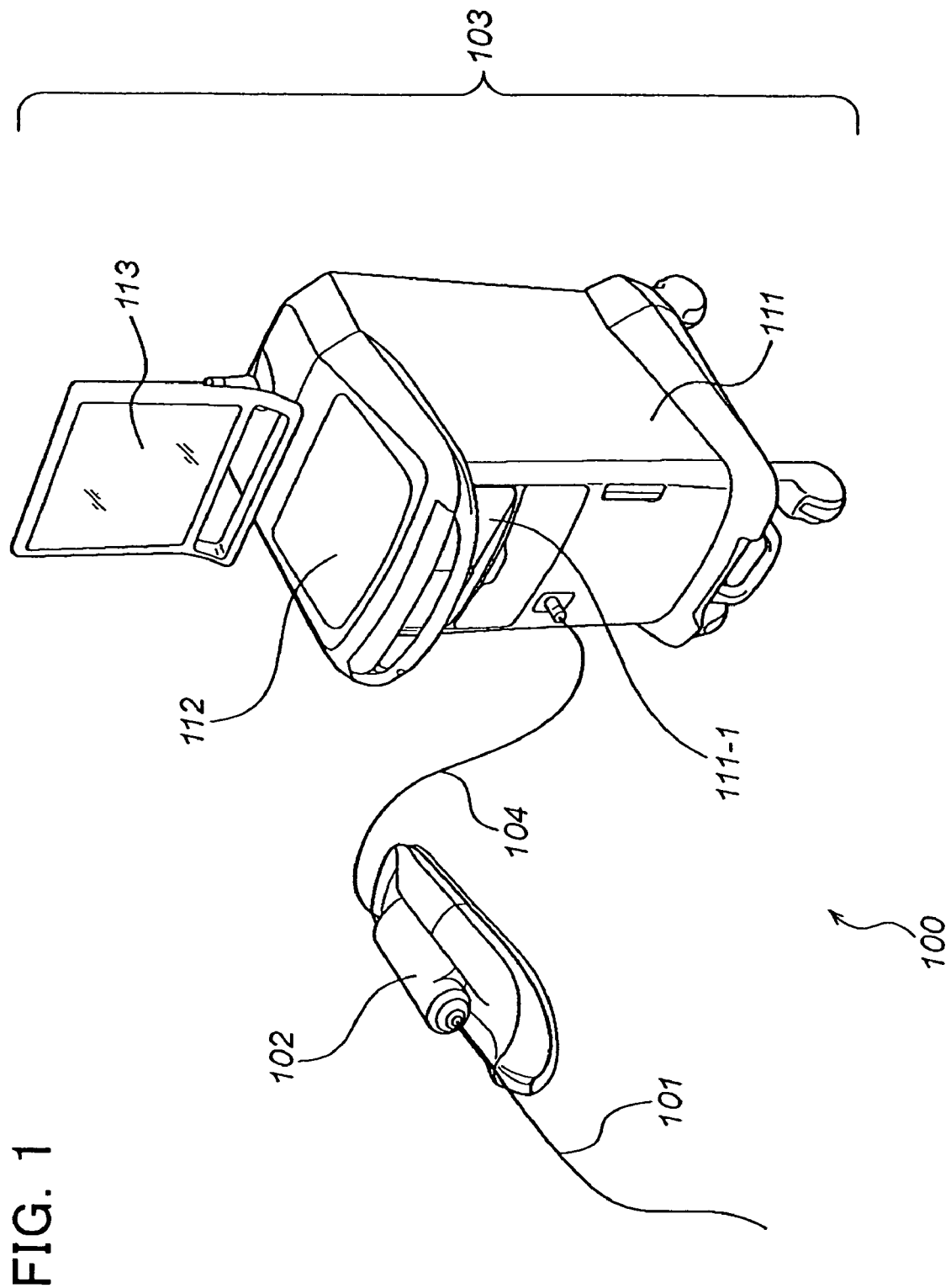
FIG. 1 is a perspective view generally illustrating aspects and features of an IVUS imaging system according to a first embodiment disclosed herein.

Referring to FIG. 1, an intravascular ultrasound (IVUS) imaging system (i.e., image diagnostic system) 100 according to one illustrated and disclosed embodiment includes a catheter section (i.e., probe) 101, a scanner & pull-back unit 102 and an operation control system 103. The scanner & pull-back unit 102 and the operation control system 103 are connected together via a signal line 104 and compose an image diagnostic apparatus.

Figure 4:
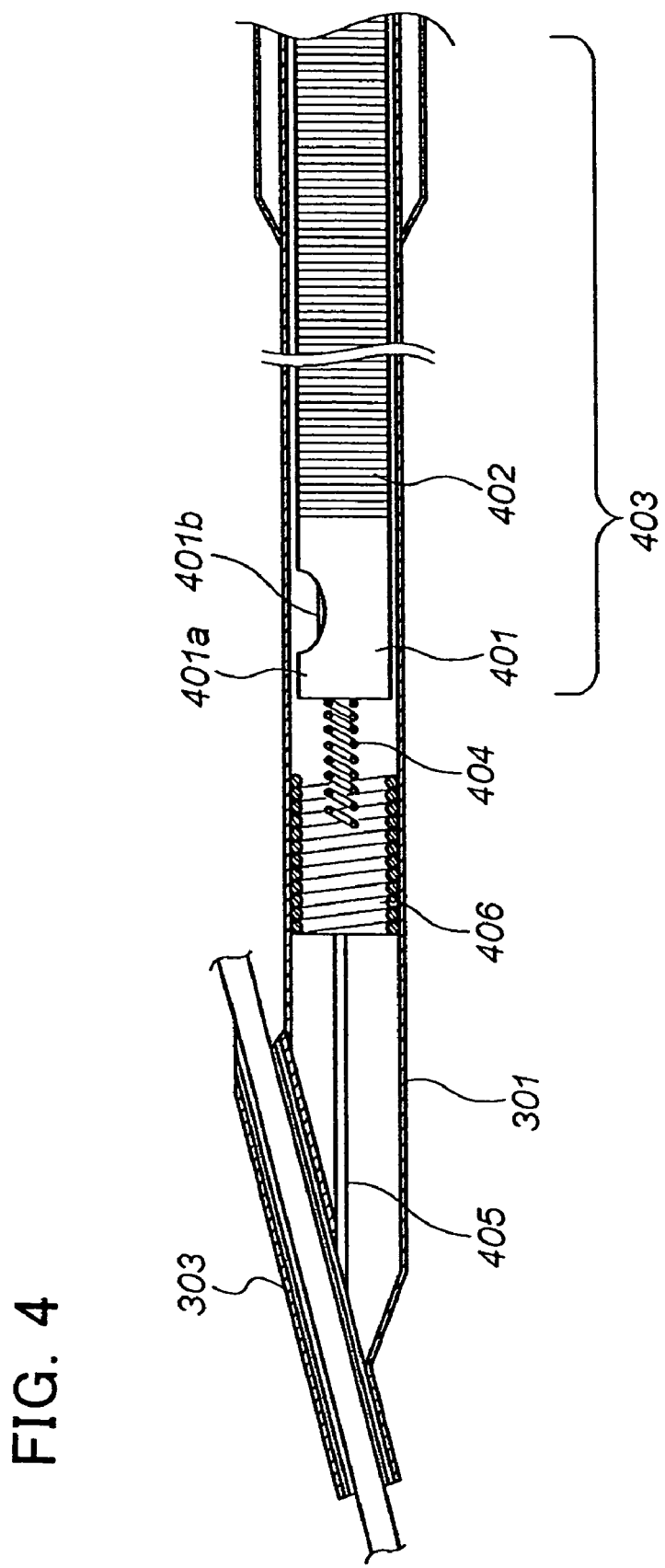
FIG. 4 is a cross-sectional view of the distal end portion of the catheter section shown in FIG. 3.

The catheter section 101 is adapted to be inserted directly into a blood vessel to measure internal conditions of the blood vessel by way of an ultrasonic transducer 401b which is shown in FIG. 4. The scanner & pull-back unit 102 controls movements of the ultrasonic transducer 401b within the catheter section 101.

The operation control system 103 operates to input various preset values upon performing an intravascular ultrasound diagnosis and to also process data acquired by a measurement and to display them as a tomographic image.

The operation control system 103 includes a main control unit 111 which performs processing of data acquired by a measurement and outputs the results of the processing, and a printer & DVD recorder 111-1 which prints the results of the processing in the main control unit 111 or records (i.e., stores) them as data.

The operation control system 103 also includes a control panel 112. Through the control panel 112, a user is able to input various values such as preset values. In addition, the operation control system 103 includes an LCD monitor 113 (i.e., display) which displays the results of the processing in the main control unit 111.

2. Aspects and Features of IVUS Imaging System

Figure 2:
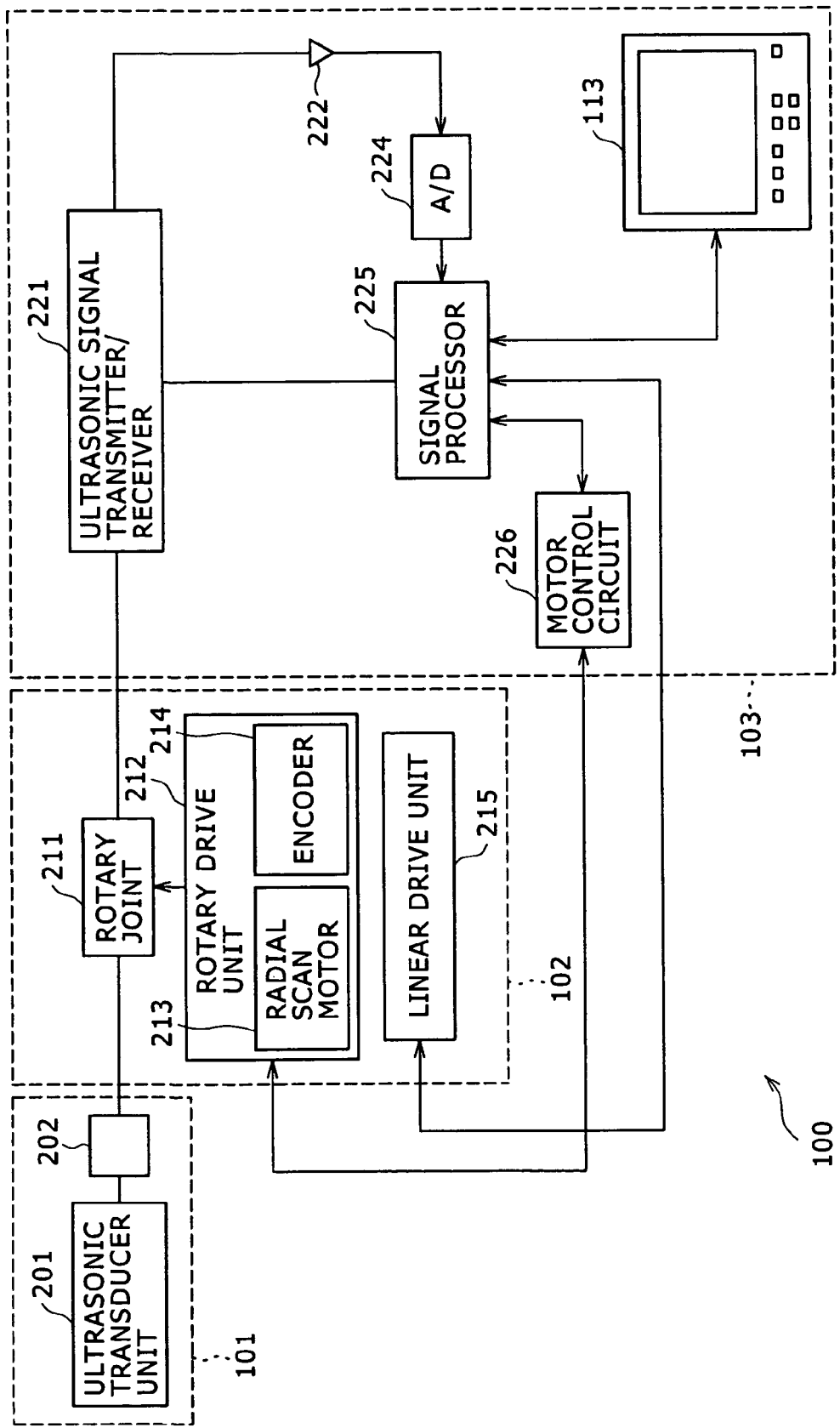
FIG. 2 is a block diagram schematically illustrating additional aspects and features of the IVUS imaging system.

FIG. 2 schematically illustrates in more detail aspects and features of the IVUS imaging system 100 illustrated in FIG. 1. The distal end of the catheter section 101 is internally provided with an ultrasonic transducer unit 201. With the distal end of the catheter section 101 inserted within a blood vessel, the ultrasonic transducer unit 201, responsive to a pulse wave transmitted by an ultrasonic signal transmitter/receiver 221, transmits ultrasound in the direction of a section of the blood vessel, and receives the reflected signals (echoes) and transmits them as ultrasonic echo signals to the ultrasonic signal transmitter/receiver 221 via a connector 202 and a rotary joint 211.

The scanner & pull-back unit 102 includes the rotary joint 211, a rotary drive unit 212 and a linear drive unit 215. The ultrasonic transducer unit 201 within the catheter section 101 is rotatably mounted by the rotary joint 211, which connects a non-rotatable block and a rotatable block with each other, and is rotationally driven by a radial scan motor 213. Rotation of the ultrasonic transducer unit 201 in a circumferential direction within the blood vessel makes it possible to detect ultrasound echo signals required for the construction of a tomographic image of the blood vessel at the predetermined position within the blood vessel.

It is to be noted that the operation of the radial scan motor 213 is controlled based on a control signal transmitted from a signal processor 225 via a motor control circuit 226. Further, each rotation angle of the radial scan motor 213 is detected by an encoder 214. Each output pulse outputted at the encoder 214 is inputted in the signal processor 225, and is used as a timing for the reading of signals to be displayed.

The scanner & pull-back unit 102 includes the linear drive unit 215 and, based on an instruction from the signal processor 225, specifies movements of the catheter section 101 in the direction of its insertion.

The ultrasonic signal transmitter/receiver 221 includes a transmission circuit and a reception circuit (not shown). Based on a control signal transmitted from the signal processor 225, the transmission circuit transmits a pulse wave to the ultrasonic transducer unit 201 in the catheter section 101.

The reception circuit, on the other hand, receives the signals based on the ultrsonic echoes from the ultrasonic transducer unit 201 in the catheter section 101. The thus-received signals are amplified by an amplifier 222.

At an A/D converter 224, the signals outputted from the amplifier 222 are sampled to produce digital data (ultrasound echo data) for one line.

Ultrasound echo data produced in line units at the A/D converter 224 are inputted into the signal processor 225. The signal processor 225 detects the ultrasound echo data, constructs tomographic images of the blood vessel at respective positions within the blood vessel, and outputs them at a predetermined frame rate to the LCD monitor 113.

3. Construction of Catheter Section

3.1 Overall Construction of Catheter Section

Figure 3:
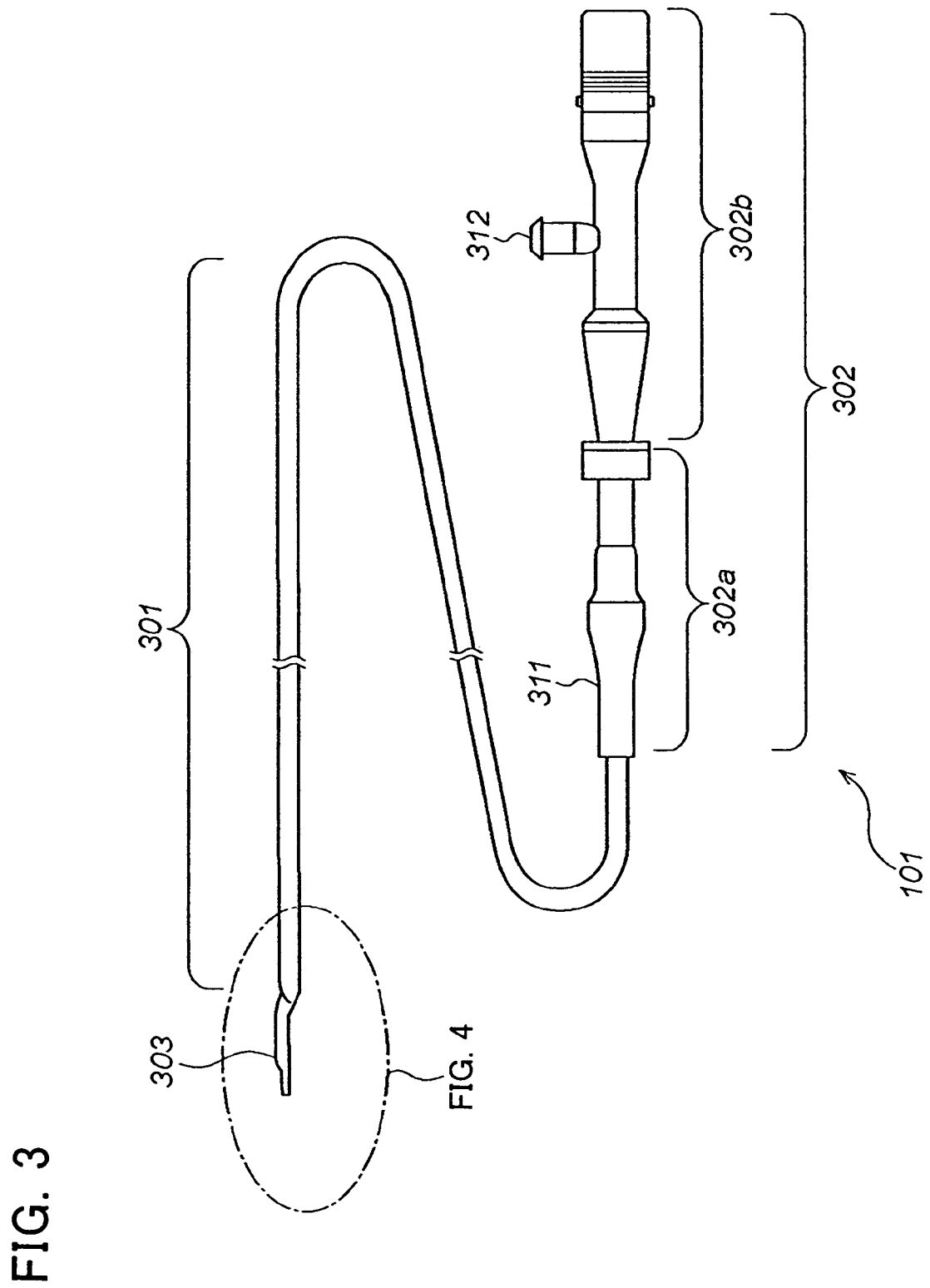
FIG. 3 is a perspective view of the overall construction of a catheter section in the IVUS imaging system.

The overall general construction of the catheter section 101 is illustrated in FIG. 3. The catheter section 101 is constructed of an elongated catheter sheath 301 adapted to be inserted into a blood vessel and a connector 302, not inserted into the blood vessel, that is arranged on the side of the user's hand to permit handling and operation by the user. A guidewire lumen 303 is provided at the distal end of the sheath 301. Within the catheter sheath 301 is a lumen which continuously extends from a connecting portion with the guidewire lumen 303 to a connecting portion with the connector 302.

The connector 302 is composed of a sheath connector 302a and a driveshaft connector 302b. The sheath connector 302a is constructed integrally with the proximal end of the catheter sheath 301. The driveshaft connector 302b is arranged on the proximal end of a driveshaft, which will be described subsequently herein, to rotatably hold the drive shaft.

An anti-kink protector 311 is arranged at a boundary portion between the sheath connector 302a and the catheter sheath 301. The arrangement of this anti-kink protector 311 makes it possible to maintain a predetermined degree of stiffness, thereby preventing any short tight twist or curl which might otherwise be caused by a sudden change in torque. The driveshaft connector 302b is provided with an injection port 312 to which a syringe (not illustrated) or the like can be attached to fill up the lumen of the catheter sheath 301 in its entirety with an ultrasound transmission fluid. The proximal end of the driveshaft connector 302b is constructed to be connected to the scanner & pull-back unit 102.

3.2 Construction of Distal End Portion of Catheter Section

FIG. 4 illustrates in more detail the distal end portion of the catheter section 101. Through the lumen of the catheter sheath 301, an imaging core 403 extends over substantially the entire length of the catheter sheath 301. The imaging core 403 is provided with an ultrasonic transducer unit 401 for transmitting and receiving ultrasound and also includes the driveshaft 402 for transmitting drive force to rotate the ultrasonic transducer unit 401. The ultrasonic transducer unit 401 is comprised of an ultrasonic transducer 401b and a housing 401a in which the ultrasonic transducer 401b is held. Ultrasound is transmitted from the ultrasonic transducer 401b toward the surrounding biotissue of a body cavity, and reflected waves from the surrounding biotissue of the body cavity are received at the ultrasonic transducer 401b.

The driveshaft 402 is constructed in the form of a coil, accommodates a signal line therein, and extends from the ultrasonic transducer 401b to the connector 302.

The ultrasonic transducer 401b possesses a rectangular or circular shape, and is formed by depositing electrodes on opposite sides of a piezoelectric member made of PZT or the like. The ultrasonic transducer 401b is arranged to assume a position around the central axis of rotation to prevent the driveshaft 402 from causing rotational fluctuations.

The housing 401a is in the form of a short cylindrical tube provided at a part thereof with a cut-off portion. Examples of materials forming the housing 401a include metal or hard resin. Examples of methods for forming the housing 401a include machining such as cutting, laser machining or pressing a tubular material to form the cut-off portion, or the desired shape may be directly obtained by injection molding, MIM (metal injection molding) or the like. The housing 401a carries the ultrasonic transducer 401b therein. The proximal end side of the housing 401a is connected with the driveshaft 402. On the distal end side of housing 401a, a resilient member 404 in the form of a short coil is arranged.

The resilient member 404 is coil-shaped wire which can be produced by forming a stainless steel wire into a coiled shape. The arrangement of the resilient member 404 on the distal end side of the housing 401a provides the imaging core 403 with improved stability upon rotation. Gold plating can be applied to a surface of the resilient member 404 or the housing 401a. As gold is a metal having high x-ray opacity, the gold plating permits visualization of the resilient member 404 in an image taken by an x-ray imaging system when the catheter sheath 301 is inserted into a body cavity. As a consequence, the user can easily ascertain the position of the ultrasonic transducer 401b.

At a boundary portion between the distal end portion of the catheter sheath 301 and the guidewire lumen 303, a discharge channel 405 is arranged to discharge out the ultrasound transmission fluid injected during priming.

A reinforcement coil 406 is arranged inside the catheter sheath 301 to assist in preventing kinking of the distal end portion of the catheter sheath 301.

The guidewire lumen 303 has a bore adapted to receive a guidewire. The guidewire is inserted beforehand in a body cavity and is utilized to guide the catheter sheath 301 to a diseased part.

The driveshaft 402 is constructed of a multiple or multi-layer, tight coil or the like having properties such that it can rotate and slide relative to the catheter sheath 301, is flexible, and can relatively smoothly transmit rotation. The multiple or multilayer, tight coil or the like may be made, for example, of a wire of a metal such as stainless steel.

Owing to the rotation of the driveshaft 402, the lumen can be observed over 360 degrees. To perform an observation over a still greater range, it is only necessary to slide the driveshaft 402 in the axial direction.

Figure 5:
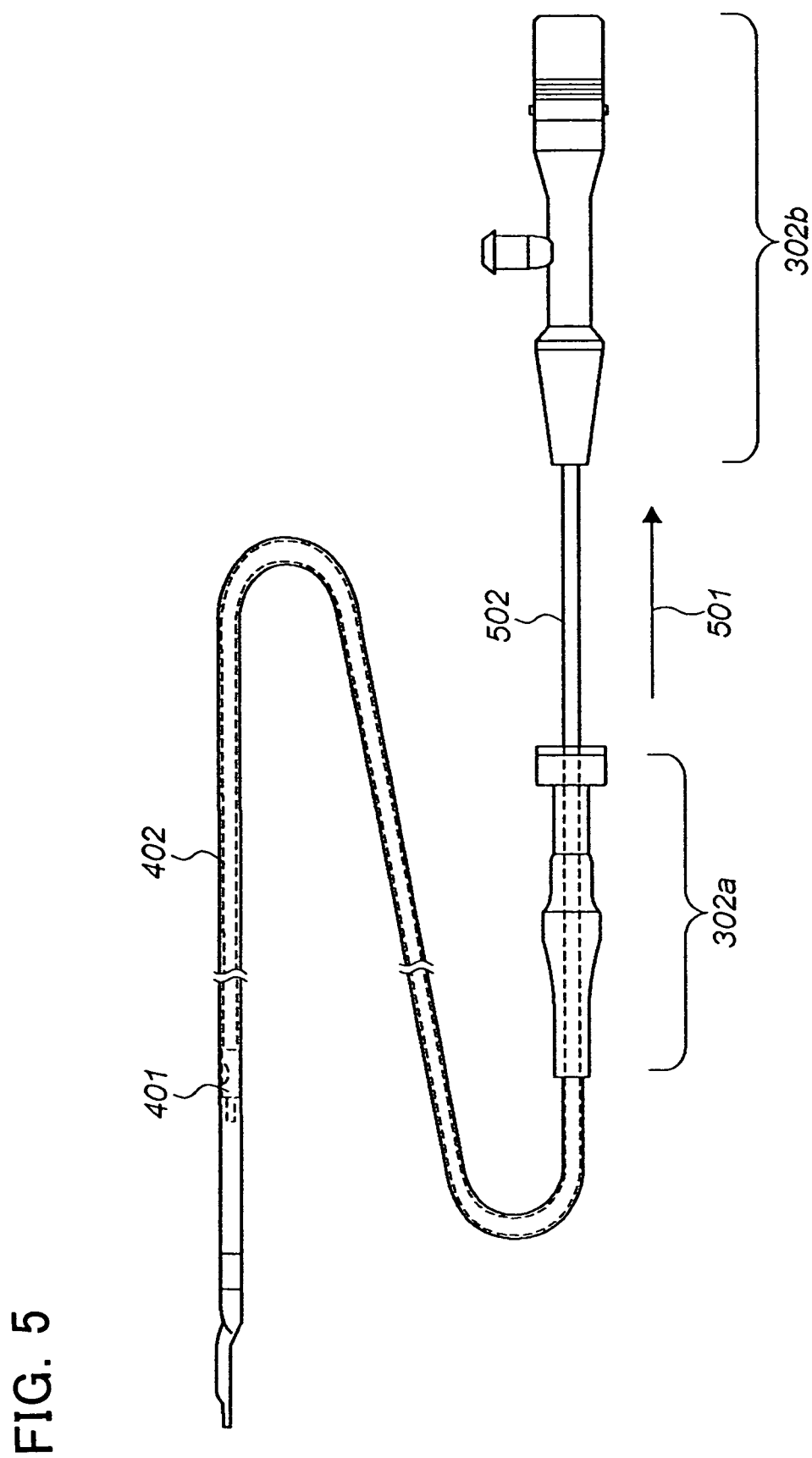
FIG. 5 is a perspective view of the catheter section showing the manner of sliding a driveshaft relative to a catheter sheath in the catheter section.

FIG. 5 schematically illustrates the manner in which the driveshaft 402 is slidably pulled back relative to the catheter sheath 301. The sliding of the driveshaft connector 302b toward its proximal end (in the direction of arrow 501) with the sheath connector 302a held fixed causes the driveshaft 402, which is accommodated within and fixed to the driveshaft connector 302b, and the ultrasonic transducer unit 401, which is fixedly secured on the distal end of the driveshaft 402, to also slide in the axial direction. This axial sliding may be effected either manually by the user or by an electrical drive. On the distal end side of the driveshaft connector 302b, a protecting inner tube 502 is arranged to avoid exposure of the driveshaft 402 which rotates at a high speed.

4. Features of the Signal Processor

Figure 6:
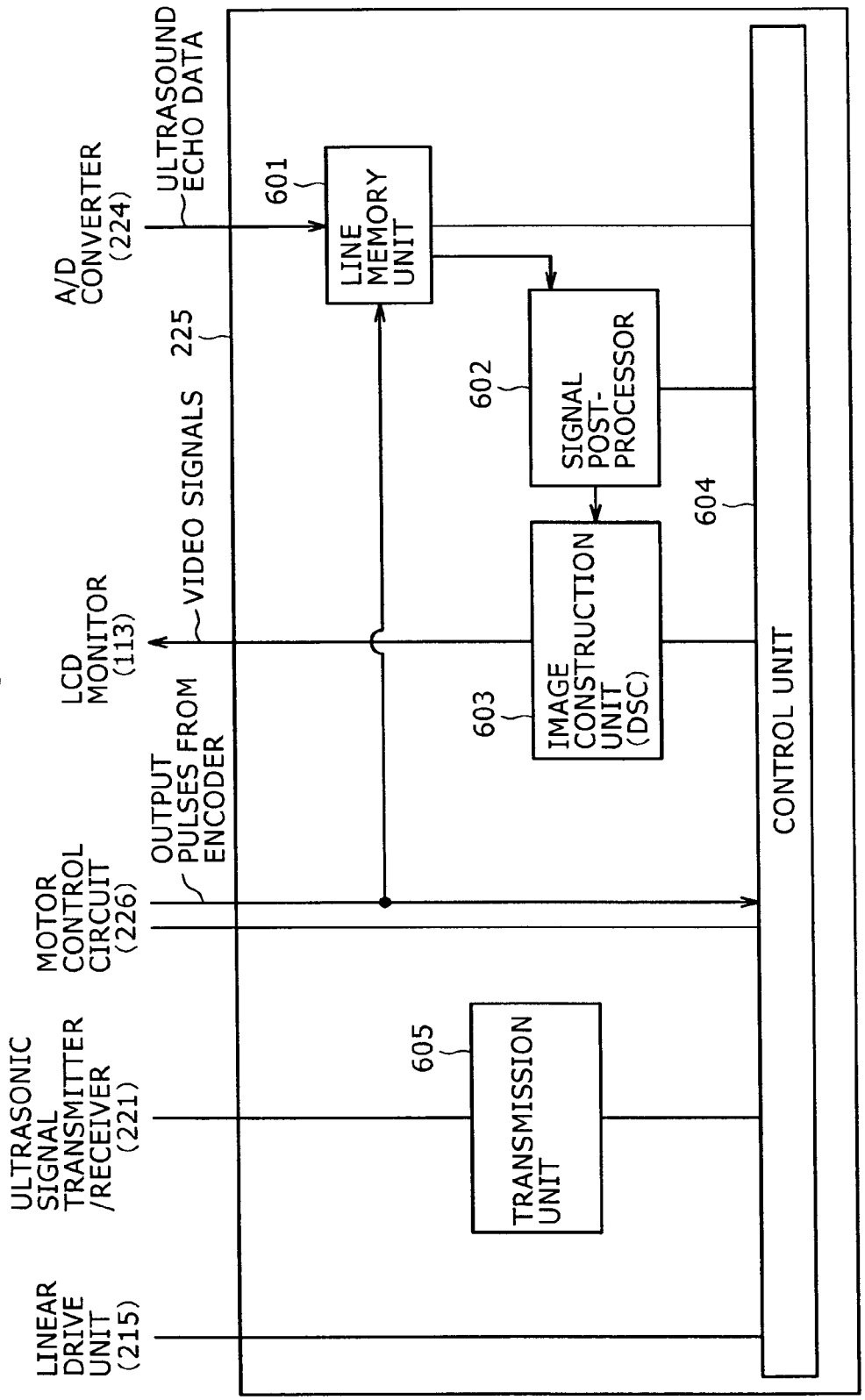
FIG. 6 is a block diagram schematically illustrating aspects of a signal processing unit in the IVUS imaging system.

Various aspects of the signal processor 225 forming a part of the operation control system 103 of the IVUS imaging system 100 are illustrated in FIG. 6. The signal processor 225 includes a control unit 604 which systematically controls the IVUS imaging system 100 in its entirety, and a transmission unit 605 which transmits operating instructions to the ultrasonic signal transmitter/receiver 221.

The signal processor 225 also includes a line memory unit 601. At the line memory unit 601, ultrasound echo data transmitted from the ultrasonic signal transmitter/receiver 221 via the amplifier 222 and the A/D converter 224 are successively received on a transmission/reception unit (line unit) basis, and are temporarily held.

The ultrasound echo data temporarily held in the line memory unit 601 is read in accordance with output pulses from the encoder 214 as needed (based on instructions from the control unit 604), and are then fed to a signal post-processor 602. Additional details about the line memory unit 601, writing operations to the line memory unit 601 and reading operations from the line memory unit 601 will be described in more detail below.

The signal post-processor 602 performs processing such as logarithmic conversion, frame correlation, gamma correction, contrast adjustment and sharpness filtering on the ultrasound echo data read from the line memory unit 601, and outputs the resulting data to an image construction unit 603.

At the image construction unit 603, streams of ultrasound echo data in the transmission/reception units (line units) of ultrasound are converted into video signals. Based on the video signals, tomographic images to be displayed on the LCD monitor 113 are constructed.

5. Operation of the Catheter Part 101 Upon Intravascular Ultrasound Diagnosis FIGS. 7A and 7B schematically illustrate movements of the catheter section 101 during an intravascular ultrasound (IVUS) diagnosis. FIG. 7A shows a section of a blood vessel 701 in which the catheter section 101 has been inserted. As described above, the ultrasonic transducer 401b is internally mounted at the distal end of the catheter section 101, and is rotated in the direction of arrow 702 by the radial scan motor 213.

From the ultrasonic transducer 401b, the transmission/reception of ultrasound is performed at respective rotation angles. Lines 1, 2, ..., 1024 indicate the transmitting directions of ultrasound at the respective rotation angles. In this embodiment, 1,024 times of transmissions/receptions are intermittently performed while the ultrasonic transducer 401b rotates over 360 degrees in a predetermined blood vessel section 701. The number of transmissions/receptions of ultrasound during 360-degree rotation is not limited specifically to 1,024, but can be set as desired. The scanning that is repeated with the transmission/reception of a signal while rotating the ultrasonic transducer 401b as described above is generally called "radial scan" or "radial scanning".

The transmissions/receptions of ultrasound are performed while advancing the catheter section through the blood vessel in the direction of arrow 703 shown in FIG. 7B.

6. Processing at the Line Memory Unit 601

6.1 Aspects of the Line Memory Unit 601 and Processing at the Line Memory Unit 601

The construction of the line memory unit 601 and a general outline of the processing occurring at the line memory unit 601 in the IVUS imaging system 100 according are described below with reference initially to FIGS. 8A-8D.

As shown in FIGS. 8A-8D, the line memory unit 601 is composed of line memories 801, 802, 803 for three lines. Ultrasound echo data are inputted in transmission/reception units (line units) to the line memory unit. The inputted ultrasound echo data are written in the line memories in synchronization with a timing of transmission/reception at the ultrasonic transducer, respectively.

Here, each writing is performed to one of the line memories other than a line memory being read, specifically the one line memory storing the oldest data therein. At this time, the oldest data which have previously been written are deleted.

On the other hand, the reading of ultrasound echo data from each line memory is performed in synchronization with a corresponding output pulse from the encoder 214. The reading is performed from one of the line memories, other than a line memory being read, specifically the one line memory storing the latest (newest) ultrasound echo data.

Figure 8A:
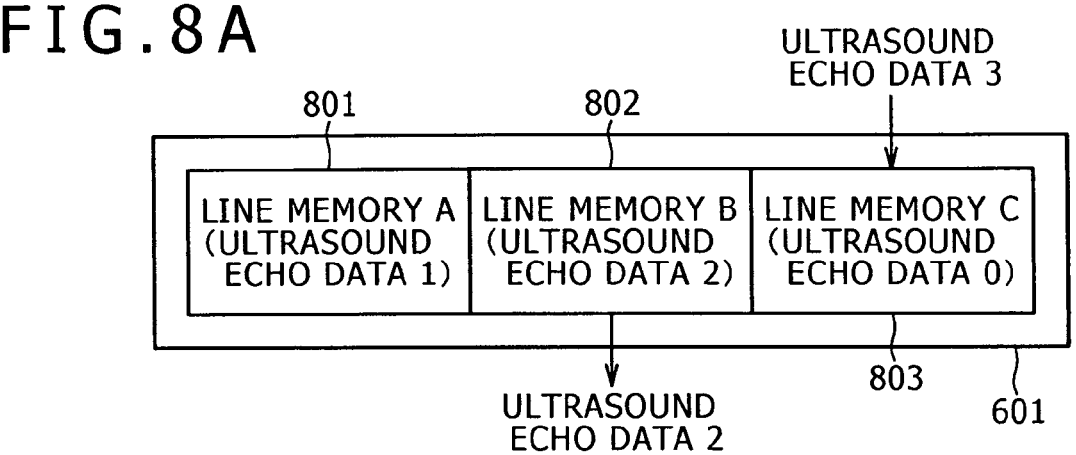
FIGS. 8A-8D are schematic illustrations of aspects of a line memory unit in the IVUS imaging system and an outline of the processing at the line memory unit.

An example will be described with reference to FIGS. 8A-8D. FIG. 8A illustrates a state in which ultrasound echo data 1 are stored in the line memory A (801), ultrasound echo data 2 are stored in the line memory B (802), and ultrasound echo data 0 are stored in the line memory C (803).

Now assume that ultrasound echo data 3 have been inputted. Supposing that no reading of ultrasound echo data is being performed from any one of the line memories at the time of the input of the ultrasound echo data 3, a determination is made as to the one of the line memories A(801) to C(803) containing the oldest ultrasound echo data.

Now assume that these ultrasound echo data become older in the order of: ultrasound echo data 2→the ultrasound echo data 1→the ultrasound echo data 0. Accordingly, it is the line memory C(803) that stores the oldest ultrasound echo data, and the ultrasound echo data 3 are hence written in the line memory C(803). The writing of the ultrasound echo data in the line memory can be controlled by a writing control unit forming a part of the control unit 604.

When an output pulse is received from the encoder 214 during the writing of the ultrasound echo data 3, reading of ultrasound echo data is initiated. Because the line memory C(803) is being written at this time, it is the line memory A(801) or the line memory B(802) that is possibly to be subjected to reading.

Now comparing the ultrasound echo data 1 stored in the line memory A(801) with the ultrasound echo data 2 stored in the line memory B(802), the ultrasound echo data 2 are newer so that the ultrasound echo data 2 stored in the line memory B(802) are read. The reading of the ultrasound echo data can be controlled by a reading control unit forming a part of the control unit 604.

Figure 8B:
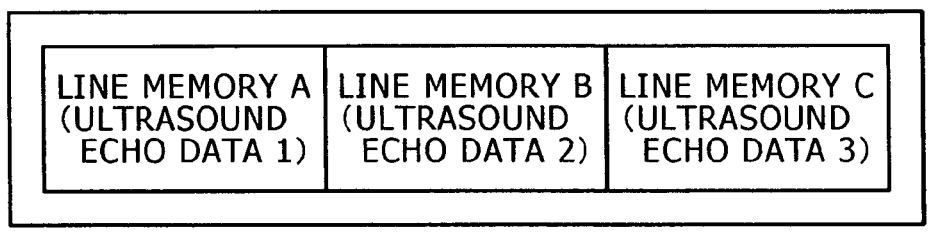

FIG. 8B illustrates a state in which the writing of the ultrasound echo data 3 and the reading of the ultrasound echo data 2 have been completed.

Figure 8C:
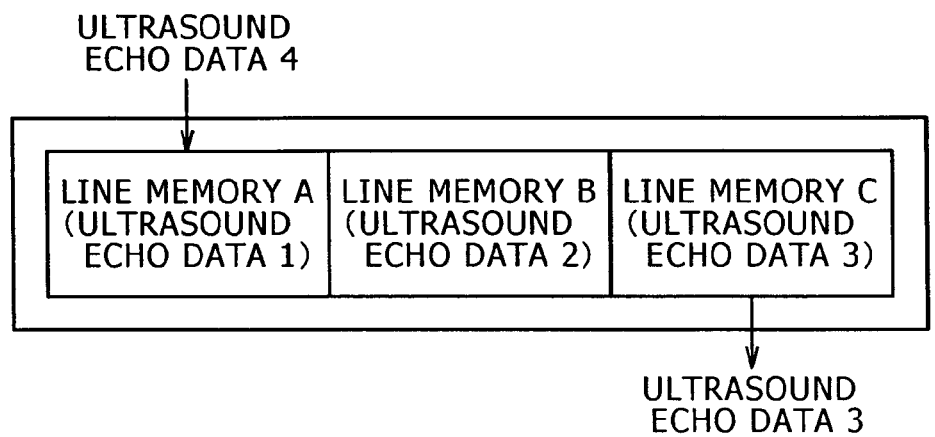

Then assume that ultrasound echo data 4 have been inputted as depicted in FIG. 8C. Supposing that no reading of ultrasound echo data is being performed from any one of the line memories at the time of the input of the ultrasound echo data, a determination is made as to which of the line memories A to C has stored therein the oldest ultrasound echo data.

As it is the line memory A that stores the oldest ultrasound echo data, the ultrasound echo data 4 are written in the line memory A.

When an output pulse is received from the encoder 214 during the writing of the ultrasound echo data 4, reading of ultrasound echo data is initiated. Because the line memory A is being written at this time, it is the line memory B or the line memory C that is possibly to be subjected to reading.

Now comparing the ultrasound echo data 2 stored in the line memory B with the ultrasound echo data 3 stored in the line memory C, the ultrasound echo data 3 are newer so that the ultrasound echo data 3 stored in the line memory C are read.

Figure 8D:
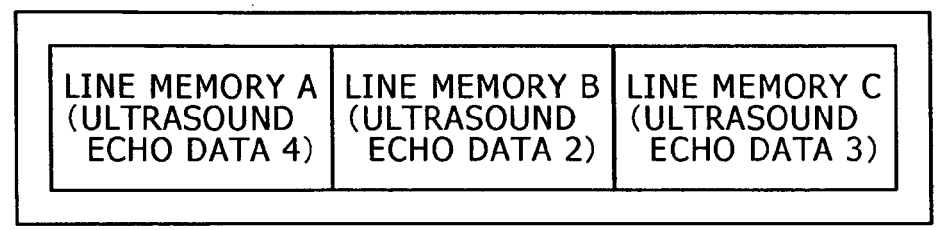

FIG. 8D illustrates a state that the writing of the ultrasound echo data 4 and the reading of the ultrasound echo data 3 have been completed. Subsequently, similar processing is repeated.

6.2 Processing for Achieving the Above-Described Signal Processing

Set forth below is a description of processing that is carried out at the line memory unit 601 to achieve the above-described signal processing. The following description is based on the assumption that the number of lines per rotation is 1,024, though as noted above this number of lines per rotation can be varied.

Figure 9:
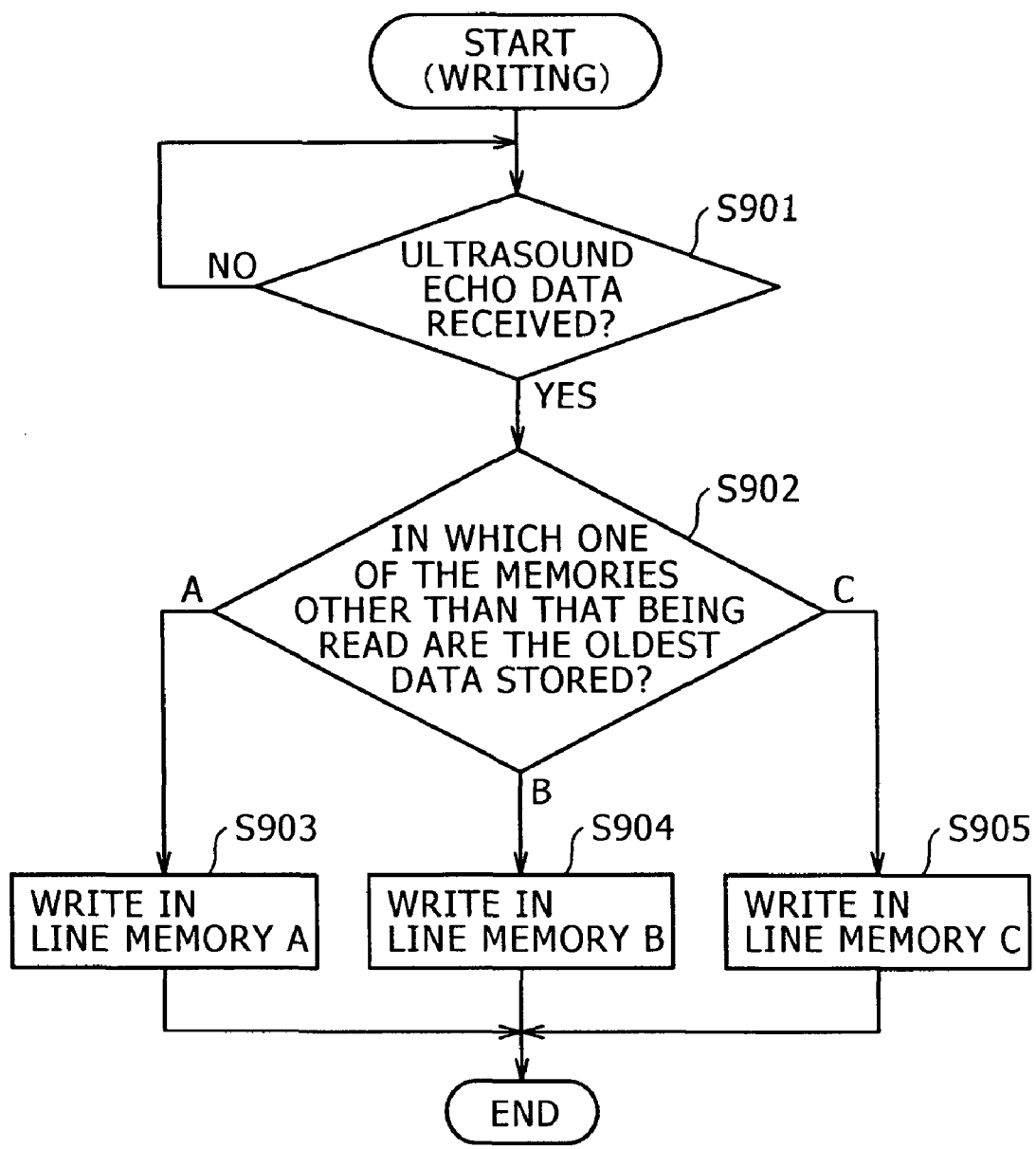
FIG. 9 is a flow chart illustrating the operational aspects of the writing processing at the line memory unit.

FIG. 9 shows the writing processing at the line memory unit 601. In step S901, a determination is made as to whether or not an input of ultrasound echo data in the line unit has been made. If the input has not been made, the processing remains in a standby mode until the input is made. Once the input is made, the process advances to step S902 where the line memory in the line memory unit 601, other than a line unit being read, storing the oldest data is determined.

If the particular line memory is determined to be the line memory A in step S902, the process advances to step S903. If the line memory is determined in step S902 to be the line memory B, the process advances to step S904, and if the line memory is determined in step S902 to be the line memory C, the process advances to step S905.

In step S903, the ultrasound echo data inputted in step S901 are written in the line memory A. In step S904, the ultrasound echo data inputted in step S901 are written in the line memory B. In step S905, the ultrasound echo data inputted in step S901 are written in the line memory C. The above processing is performed whenever ultrasound echo data are inputted.

Figure 10:
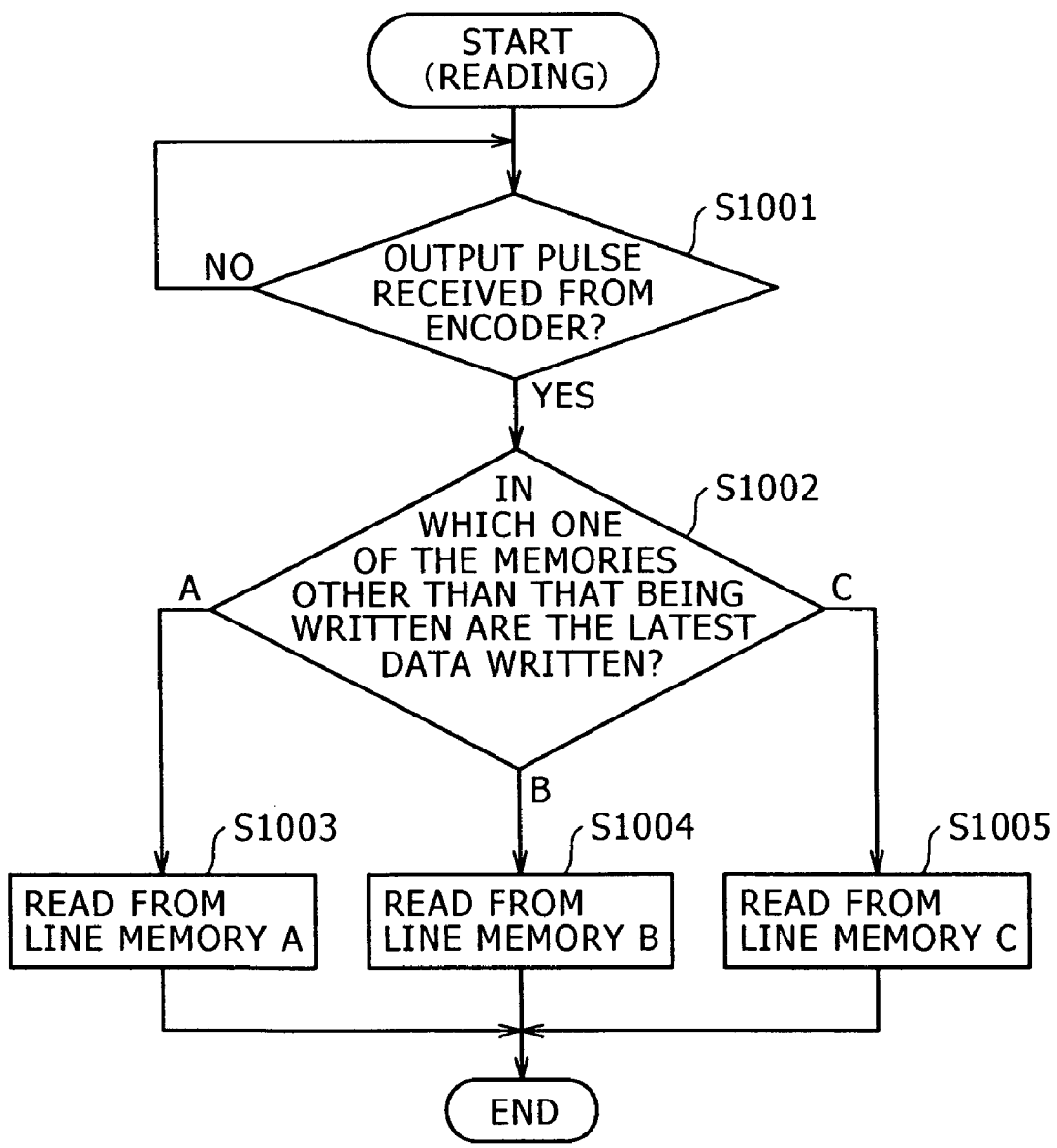
FIG. 10 is a flow chart showing operational aspects of the reading processing at the line memory unit.

FIG. 10 is a flow chart showing the flow of reading processing at the line memory unit 601. In step S1001, a determination is made as to whether or not an output pulse from the encoder 214 has been received. If an output pulse has not been received, the process remains standing by until it is received. If the output pulse has been received, on the other hand, the process advances to step S11002 in which it is determined the one of the line memories in the line memory unit 601, other than that being subjected to writing processing, storing the latest (newest) data.

If the particular one line memory is determined to be the line memory A in step S1002, the process then advances to step S1003. If it is determined in step S1002 to be the line memory B, the process advances to step S1004, and if it is determined in step S1002 to be the line memory C, the process advances to step S1005.

In step S1003, the ultrasound echo data stored in the line memory A are read. In step S1004, the ultrasound echo data stored in the line memory B are read. In step S1005, the ultrasound echo data stored in the line memory C are read. The above processing is performed whenever ultrasound echo data are inputted.

6.3 Examples of the Writing/Reading Processing at the Line Memory Unit 601

Examples of the writing and reading processing at the line memory unit 601 are described below with reference to FIGS. 11, 12A and 12B.

6.3.1 When Synchronized

Figure 11:
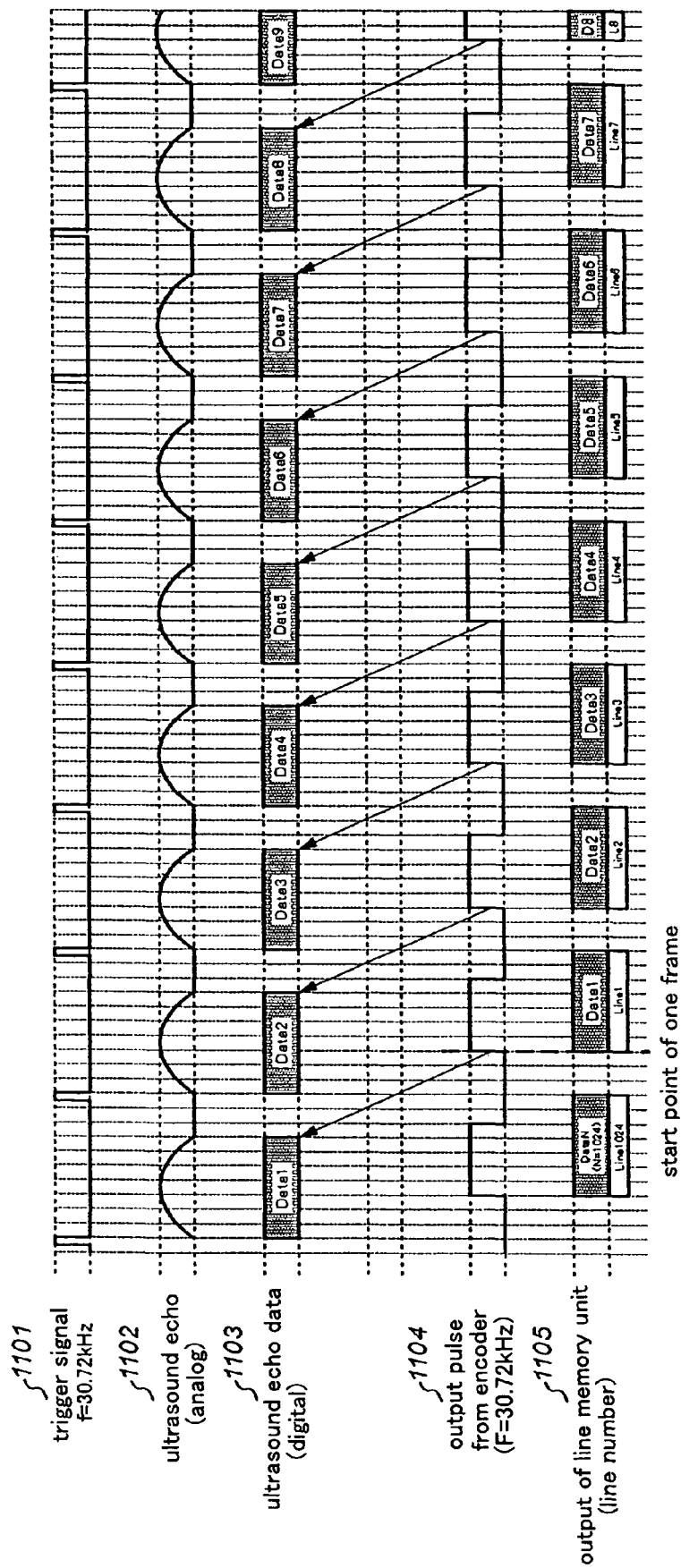
FIG. 11 is a timing chart illustrating when output pulses from an encoder and a transmission/reception timing of an ultrasonic transducer are in synchronization.

FIG. 11 is a timing chart when the output pulses from the encoder 214 and the timing of transmission/reception at the ultrasonic transducer are in synchronization. In this figure, numeral 1101 indicates the timing of trigger signals which control the timing of transmission at the ultrasonic transducer.

Numeral 1102 indicates the timing of reception of reflected waves (ultrasound echoes) from a surrounding biotissue of a body cavity in response to ultrasound transmitted based on the trigger signals 1101. Numeral 1103 designates the production timing of ultrasound echo data produced based on the ultrasound echoes.

On the other hand, numeral 1104 indicates the timing of the output pulses from the encoder 214. Further, numeral 1105 indicates the timing of reading at the line memory unit 601.

When the output pulses from the encoder 214 and the timing of transmission/reception at the ultrasonic transducer are in synchronization as shown in FIG. 11, the ultrasound echo data written in the line memory unit 601 and the data read by the reading control unit are in agreement exactly.

6.3.2 When Not Synchronized (when the Radial Scan Motor is Delayed Relative to the Timing of Transmission/Reception)

Figure 12A:
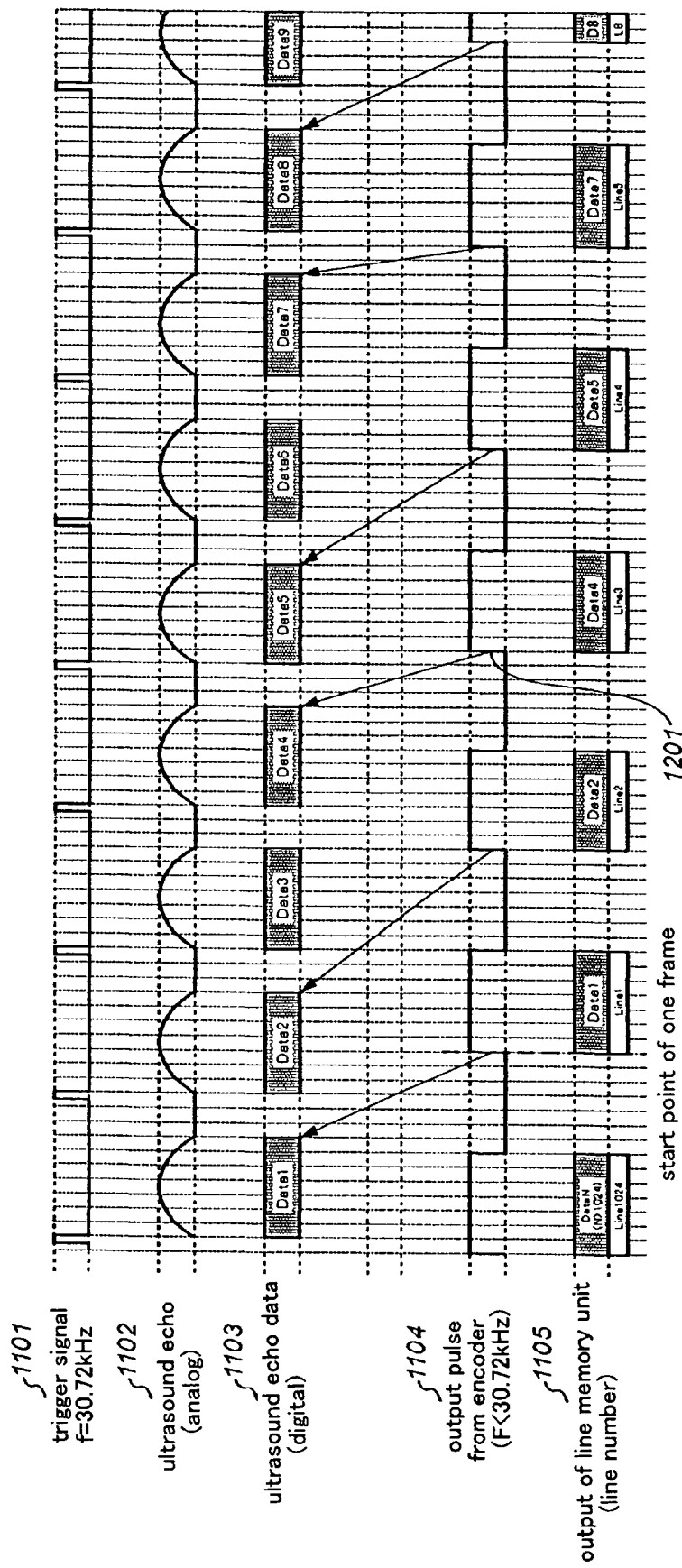
FIG. 12A is a timing chart illustrating when output pulses from the encoder and a transmission/reception timing of the ultrasonic transducer are out of synchronization.

FIG. 12A is a timing chart illustrating a situation in which the output pulses from the encoder 214 and the timing of transmission/reception at the ultrasonic transducer are out of synchronization. FIG. 12A shows that the output pulses from the encoder 214 are delayed relative to the timing of production of ultrasound echo data for a delay or the like of the radial scan motor.

Specifically, FIG. 12A shows a state in which, because the output pulses from the encoder 214 are delayed relative to the timing of production of ultrasound echo data, the reading of Data 4 is performed without effecting the reading of Data 3.

In other words, despite the production of Data 3 as ultrasound echo data (1103), Data 4 are produced and stored in the lime memory unit 601 before Data 3 are read. At the time (timing 1201) that an output pulse from the encoder 214 has been received, the latest ultrasound echo data are, therefore, determined to be Data 4 instead of Data 3. As a result, Data 3 are not read but Data 4 are read.

It is to be noted that Data 3 will not be used for the construction of a tomographic image because they will be overwritten by ultrasound echo data to be produced subsequently.

6.3.3. When Not Synchronized (when the Radial Scan Motor is Advanced Relative to the Timing of Transmission/Reception)

FIG. 12B is a timing chart illustrating another situation in which the output pulses from the encoder 214 and the timing of transmission/reception at the ultrasonic transducer are out of synchronization. Here though, FIG. 12B shows that the output pulses from the encoder 214 are advanced relative to the timing of production of ultrasound echo data for an advance or the like of the radial scan motor.

Specifically, FIG. 12B shows a state in which, because the output pulses from the encoder 214 are advanced relative to the timing of production of ultrasound echo data, the production of ultrasound echo data as Data 4 has not been completed at the time that Data 4 are supposed to be read. Therefore, the reading of Data 3 is performed again.

In other words, at the time (1202) that an output pulse from the encoder 214 has been received, the latest ultrasound echo data are determined to be Data 3 and so the reading of Data 3 is performed again.

As is evident from the above description, the IVUS imaging system according to this embodiment makes it possible to perform appropriate reading of ultrasound echo data in accordance with the rotation cycle of the probe during radial scanning even when synchronization does not exist between the rotation cycle of the probe in the radial scanning and the transmission/reception cycle of ultrasound from the probe.

As a result, it is possible to reduce or eliminate the difficulties encountered in other systems mentioned above in which a tomographic image may be displayed blurred in the circumferential direction or may be displayed while slowly turning.

Second Embodiment

The description set forth above concerning the first embodiment describes the processing at the signal processor when the radial scanning by the ultrasonic transducer is made faster in the IVUS imaging system. However, the disclosed system and method are not limited specifically to IVUS imaging systems. Indeed, the disclosure herein is also applicable to other image diagnostic systems. The description which follows described application of the disclosed subject matter to an optical coherence tomography (OCT) imaging system.

1. Diagnostic Principle of OCT Imaging System

For background purposes, set forth below is a general description of the diagnostic principle of the OCT imaging system. Because light is electromagnetic radiation, it generally has the property that beams of light interfere with each other when they are superimposed. The interference property defining whether light interferes readily or hardly is called "coherence." In general OCT imaging systems, low-coherence light (i.e., short-coherence light) of low interference property is used.

Figures 13A, 13B:
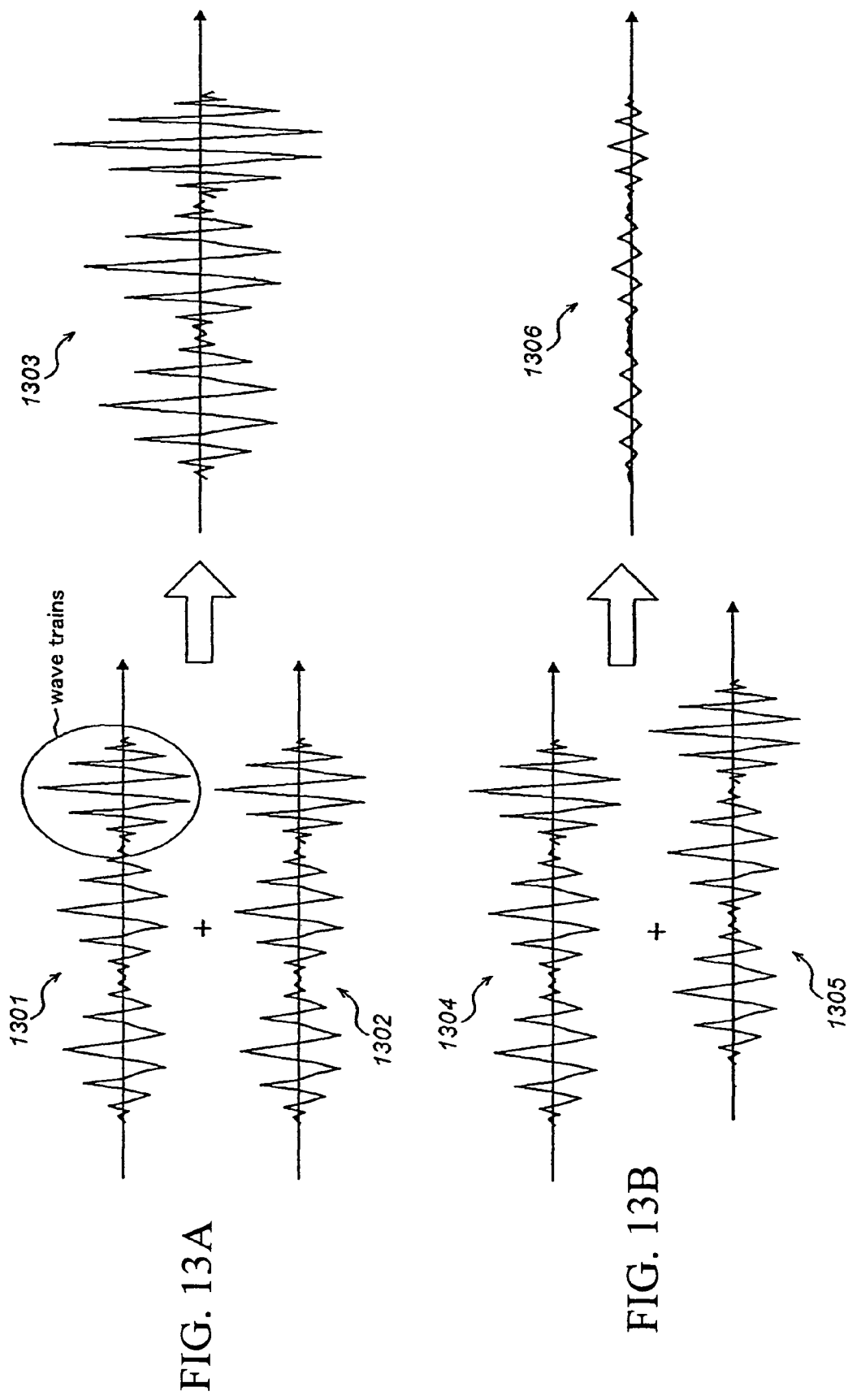
FIGS. 13A and 13B are waveform diagrams illustrating the principle of a measurement by an OCT imaging system according to another embodiment disclosed herein.

Referring to FIG. 13A, when time is plotted along the abscissa and electric field is plotted along the ordinate, low-coherence light becomes random signals as indicated at 1301 and 1302. Individual peaks in the figure are called "wave trains", and have their own, mutually-independent phases and amplitudes. When the same wave trains (1301 and 1302) overlap with each other as in FIG. 13A, the wave trains interfere with each other to intensify each other as represented at 1303. On the other hand, when there is a slight delay in time between wave trains (1304 and 1305 in FIG. 13B), the wave trains cancel each other so that no interference is observed as represented at 1306 in FIG. 13B.

The OCT imaging system makes use of these properties, and the basic principle of the system is illustrated in FIG. 14. As illustrated, light emitted from a low-coherence light source 1401 is split into a reference path and a sampling path at a beam splitter 1404. One of the resulting light beams which is split into the reference path is then directed toward a reference mirror 1402 and another resulting light beam which is split into the sampling path is then directed toward an imaging target (i.e. blood vessel wall) 1403. At this time, reflected light returning from the imaging target includes light reflected on the surface of the imaging target, light reflected at shallow points in the imaging target, and light reflected at deep points in the imaging target.

As the incident light is low-coherence light, the reflected light on which interference can be observed is, however, only the reflected light from a reflection surface located at a position apart by a distance of $L+\Delta L/2$ from the beam splitter 1404, where L represents the distance from the beam splitter 1404 to the reference mirror 1402 and $\Delta L$ represents a coherence length.

By changing the distance of the reference path from the beam splitter 1404 to the reference mirror 1402, it is possible to selectively detect at a detector 1405 the reflected light from a reflection surface, which corresponds to the thus-changed distance, in the imaging target. A tomographic image can then be constructed by visualizing internal structural information of the imaging target on the basis of the intensities of reflected light beams corresponding to such respective distances.

2. General Overall Construction of OCT Imaging System

The general overall construction of the OCT imaging system is similar to that of the IVUS imaging system described above and shown in FIG. 1 and so a detailed description of the construction is not repeated.

3. Aspects and Features of OCT Imaging System

Figure 15:
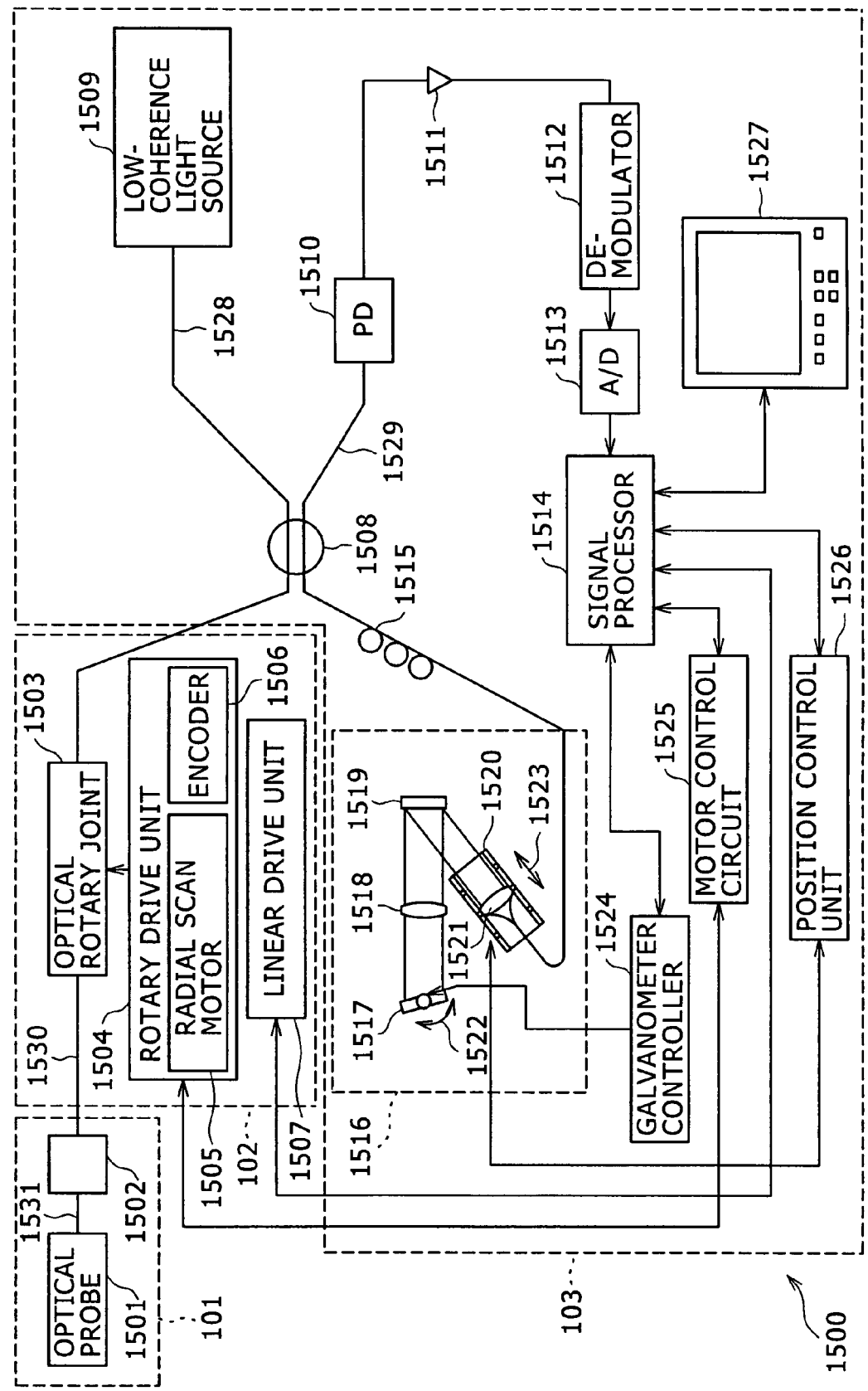
FIG. 15 is a block diagram depicting operational aspects of the OCT imaging system.

FIG. 15 illustrates features and aspects associated with the OCT imaging system (i.e. image diagnostic system) 1500 according to this illustrated and disclosed embodiment. The system includes a low-coherence light source 1509 such as a light emitting diode of ultra-high intensity. The low-coherence light source 1509 outputs low-coherence light having a wavelength around 1,310 nm, and the outputted low-coherence light shows interference property only in such a short distance range that its coherence length approximately ranges from several micrometers to over ten micrometers.

When the light is split into two and the resulting beams of light are combined back, the combined light is, therefore, detected as coherent light when the difference between the two optical path lengths from the splitting point to the combining point falls within a short distance range around 17 µm, but no coherent light is detected when the difference in optical path length is greater than the above-described range.

The light from the low-coherence light source 1509 impinges on a proximal end face of a first single mode fiber 1528, and is transmitted toward its distal end face. At an optical coupler 1508 arranged midway along the first single mode fiber 1528, the first single mode fiber 1528 is optically coupled with a second single mode fiber 1529 which composes the reference path. Therefore, the light transmitted through the first single mode fiber 1528 is split into two by the optical coupler 1508 and the resulting two beams of light (i.e., the sample path and the reference path) are transmitted further.

On a more distal end side of the first single mode fiber 1528 than the optical coupler 1508, an optical rotary joint 1503 is arranged to connect a non-rotatable block and a rotatable block with each other such that light can be transmitted.

Further, an optical-probe connector 1502 is detachably connected to a distal end of a third single mode fiber 1530 in the optical rotary joint 1503. Via the connector 1502, the light from the low-coherence light source 1509 is transmitted to a fourth single mode fiber 1531 which is inserted in an optical probe (i.e. catheter) 1501 and is rotationally drivable.

The transmitted light is irradiated from the distal end side of the optical probe 1501 toward a surrounding biotissue of a body cavity while performing radial scanning. A portion of reflected light scattered on a surface or interior of the biotissue is collected by the optical probe 1501, and returns toward the first single mode fiber 1528 through the reverse optical path. A portion of the thus-collected, reflected light is transferred by the optical coupler 1508 to the side of the second single mode fiber 1529, and is introduced into a photodetector (for example, photodiode 1510) from an end of the second single mode fiber 1529. It is to be noted that the rotatable block side of the optical rotary joint 1503 is rotationally driven by a radial scan motor 1505 of a rotary drive unit 1504. Further, rotation angles of the radial scan motor 1505 are detected by an encoder 1506. The optical rotary joint 1503 is provided with a linear drive unit 1507 which, based on an instruction from a signal processor 1514, controls movement of the catheter section 101 in the direction of its insertion.

On the more distal end side of the second single mode fiber 1529 than the optical coupler 1508, an optical path length (OPL) varying mechanism 1516 is arranged to vary the optical path length of reference light.

This OPL varying mechanism 1516 is provided with a first OPL varying means for varying the optical path length, which corresponds to the examinable range in the direction of the depth of the biotissue, at high speed and also with a second OPL varying means for varying the optical path length by a length equivalent to a variation in the length of a new optical probe to adjust the variation when the new optical probe is used as a replacement (so generally intravascular probes are disposable for infection prevention).

Opposing the distal end of the second single mode fiber 1529, a grating (diffraction grating) 1519 is arranged via a collimator lens 1521 which is mounted together with the distal end of the second single mode fiber 1529 on a single axis stage 1520 and is movable in the direction indicated by arrow 1523. Further, a galvanometer mirror 1517 which is rotatable over small angles is mounted as the first OPL varying means via the grating 1519 and an associated lens 1518. This galvanometer mirror 1517 is rotated at high speed in the direction of arrow 1522 by a galvanometer controller 1524.

The galvanometer mirror 1517 serves to reflect light by its mirror, and functions as a reference mirror. The galvanometer mirror 1517 is constructed such that its mirror mounted on a movable part of its galvanometer is rotated at high speed by applying an a.c. drive signal to the galvanometer.

Described more specifically, by applying a drive signal to the galvanometer from the galvanometer controller 1524 and rotating the galvanometer at high speed in the direction of arrow 1522 with the drive signal, the optical path length of reference light is varied at high speed by an optical path length equivalent to a detection range in the direction of the depth of the biotissue. A single cycle of variations in optical path length (single scanning) becomes a cycle that produces interference light data for a single line data (in line unit).

On the other hand, the single axis stage 1520 forms the second OPL varying means having a variable OPL range just enough to adjust a variation in the optical path length of a new optical probe when the optical probe 1501 is replaced by the new (i.e., another) optical probe. In addition, the single axis stage 1520 is also able to function as an adjustment means for adjusting an offset. Even when the distal end of the optical probe 1501 is not in close contact with a surface of the biotissue, for example, the optical probe can still be set in such a state as interfering from a position on the surface of the biotissue by slightly varying the optical path length with the single axis stage 1520.

The light varied in the optical path length by the OPL varying mechanism 1516 is combined with the light, which has returned from the first single mode fiber 1528, at the optical coupler 1508 arranged midway along the second single mode fiber 1529, and the combined light is received at the photodiode 1510.

The light received at the photodiode 1510 is amplified by an amplifier 1511, and is then inputted into a demodulator 1512. At the demodulator 1512, demodulation processing is performed to extract only the signal portion of the interfered light, and the output of the demodulator 1512 is inputted into an A/D converter 1513.

At the A/D converter 1513, interference light signals are sampled as much as for 200 points to produce digital data (interference light data) for one line. The sampling frequency is a value obtained by dividing with 200 the time required for a single scan of the optical path length.

The interference light data in the line unit, which have been produced at the A/D converter 1513, are inputted into the signal processor 1514. At this signal processor 1514, the interference light data in the direction of the depth are converted into video signals to constitute tomographic images at respective positions in the blood vessel. These tomographic images are then outputted at a predetermined frame rate to an LCD monitor 1527.

The signal processor 1514 is connected with a position control unit 1526. The signal processor 1514 performs control of the position of the single axis stage 1520 via the position control unit 1526. In addition, the signal processor 1514 is also connected with a motor control circuit 1525 to control rotational drive by the radial scan motor 1505.

Further, the signal processor 1514 is also connected with the galvanometer controller 1524 which controls the scanning of the optical path length of the reference mirror (galvanometer mirror). The galvanometer controller 1524 outputs a drive signal to the signal processor 1514, and based on this drive signal, the motor control circuit 1525 is synchronized with the galvanometer controller 1524. This synchronization, however, may be offset due to a variation or the like in torque inside the blood vessel or the like.

4. Construction of Catheter Section

Figure 16:
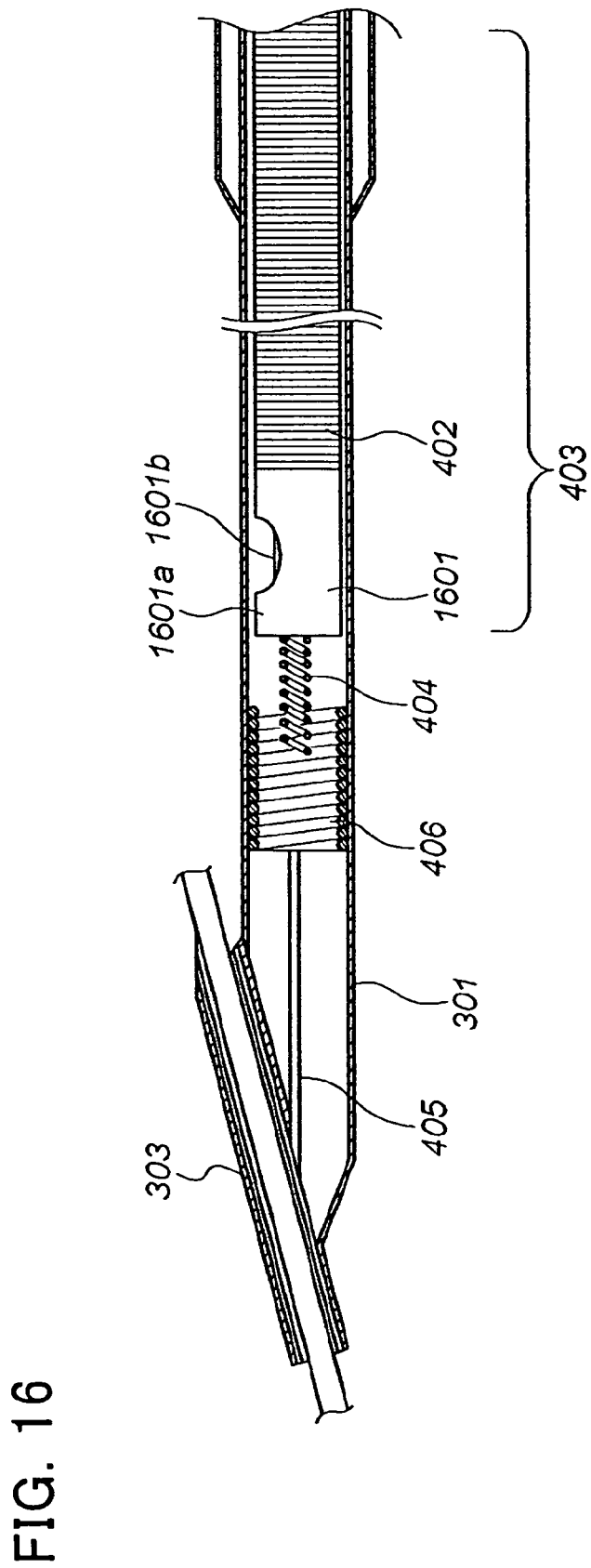
FIG. 16 is a cross-sectional view of a distal end portion of a catheter section in the OCT imaging system.

The overall construction of the catheter section 101 in the OCT imaging system is the same as the overall construction of the catheter section in the IVUS imaging system described above and so a detailed description of such overall construction is not repeated here. With reference to FIG. 16, the following describes differences associated with the construction of the distal end portion of the catheter section 101 in the OCT imaging system 1500.

An optical probe 1601 which irradiates/receives low-coherence light is arranged within the lumen of the catheter sheath 301. The optical probe 1601 is provided with a prism or mirror 1601b to perform lateral irradiation. The optical probe 1601 includes the prism or mirror 1601b and a housing 1601a in which is held the prism or mirror 1601b. The optical probe 1601 irradiates the low-coherence light toward a surrounding biotissue of a body cavity from the prism or mirror 1601b, and receives the reflected light from the surrounding biotissue of the body cavity through the prism or mirror 1601b.

An optical fiber is disposed through the drive shaft 402, and extends from the housing 1601a to the connector 1502. As the advance injection of physiological saline (priming work) is not absolutely needed in the OCT imaging system according to this embodiment, the priming discharge channel 405 formed at the boundary portion between the distal end portion of the catheter sheath 301 and the guidewire lumen 303 in the IVUS imaging system described above may be omitted.

5. Features of the Signal Processor

Features associated with the signal processor 1514 in the OCT imaging system 1500 are illustrated in FIG. 17. The signal processor includes a control unit 1704 that systematically controls the OCT imaging system 1500 in its entirety. The signal processor also includes a line memory unit 1701 at which interference light data transmitted from the photodiode 1510 via the demodulator 1512 and the A/D converter 1513 are successively received in cycle units of variations in optical path length (i.e., scanning line units), and are temporarily held.

The interference light data temporarily held in the line memory unit 1701 are read in accordance with output pulses from the encoder 1506 as needed (based on instructions from the control unit 1704), and are then fed to a correction unit 1702 as a signal post-processor. Additional details about the line memory unit 1701, including the writing operations to the line memory unit 1701 and the reading operations from the line memory unit 1701, will be described below in more detail.

The correction unit 1702 performs processing such as frame correlation, gamma correction, contrast adjustment and sharpness filtering on the interference data read from the line memory unit 1701, and outputs the resulting data to an image construction unit 1703.

At the image construction unit 1703, streams of interference light data in scanning units along the optical path length by low-coherence light (line units) are converted into video signals. Based on the video signals, tomographic images to be displayed on the LCD monitor 1527 are constructed.

6. Processing at the Line Memory Unit 1701

6.1 Features of the Line Memory Unit 1701 and Processing at the Line Memory Unit 1701

FIGS. 18A-18D schematically illustrate the construction of the line memory unit 1701 in the OCT imaging system 1500 according to this embodiment and provide a general outline of the processing at the line memory unit 1701.

As shown in these figures, the line memory unit 1701 is composed of line memories (1801, 1802, 1803) for three lines. Interference light data are inputted in OPL scanning units (line units) to the line memory unit 1701. The inputted interference light data are written in the line memories.

Here, each writing is performed to the one of the line memories, other than that being read, storing the oldest interference light data. At this time, the oldest interference light data which have already been written are deleted.

On the other hand, the reading of interference light echo data from each line memory is performed in synchronization with a corresponding output pulse from the encoder 1506. The reading is performed from the one of the line memories, other than that being read, storing the latest (newest) interference light data.

Figure 18A:
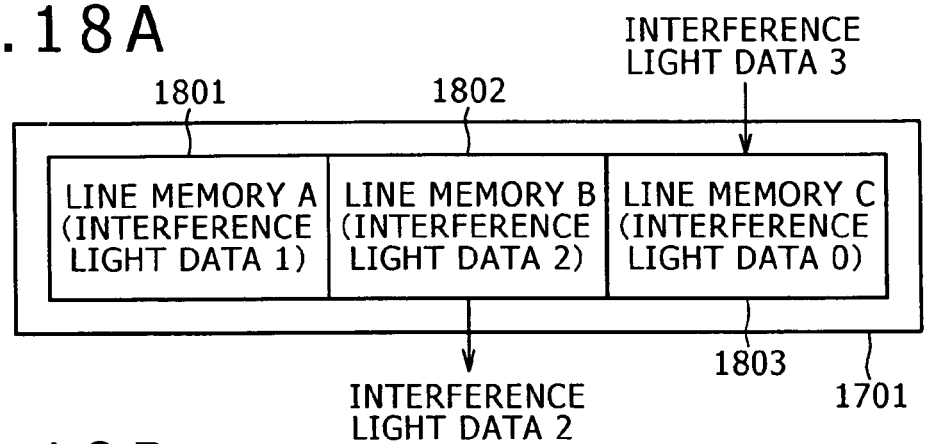
FIGS. 18A-18D are schematic illustrations of aspects of a line memory unit in the OCT imaging system and the outline of processing at the line memory unit.

An example will be described with reference to FIGS. 18A-18D. FIG. 18A illustrates a state in which interference light data 1 are stored in the line memory A(1801), interference light data 2 are stored in the line memory B(1802), and interference light data 0 are stored in the line memory C(1803).

Now assume that interference light data 3 have been inputted. Supposing that no reading of interference light echo data is being performed from any one of the line memories at the time of the input of the interference light data 3, a determination is made as to in which one of the line memories A(1801) to C(1803) contains the oldest interference light data.

Now assume that these interference light data become older in the order of the interference light data 2→the interference light data 1→the interference light data 0 (oldest). Accordingly, it is the line memory C(1803) that stores the oldest interference light data, and the interference light data 3 are hence written in the line memory C(1803). The writing of interference light data in the line memory can be controlled by a writing control unit forming a part of the control unit.

When an output pulse is received from the encoder 1506 during the writing of the interference light data 3, reading of interference light data is initiated. Because the line memory C(1803) is being written at this time, it is the line memory A(1801) or the line memory B(1802) that is possibly to be subjected to reading.

Now comparing the interference light data 1 stored in the line memory A(1801) with the interference light data 2 stored in the line memory B(1802), the interference light data 2 are newer and so the interference light data 2 stored in the line memory B(1802) are read. The reading of the interference light data in the line memory can be controlled by a reading control unit forming a part of the control unit.

Figure 18B:
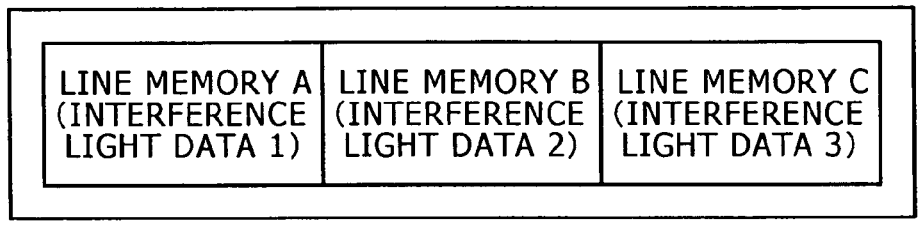

FIG. 18B illustrates a state in which the writing of the interference light data 3 and the reading of the interference light data 2 have been completed.

Figure 18C:
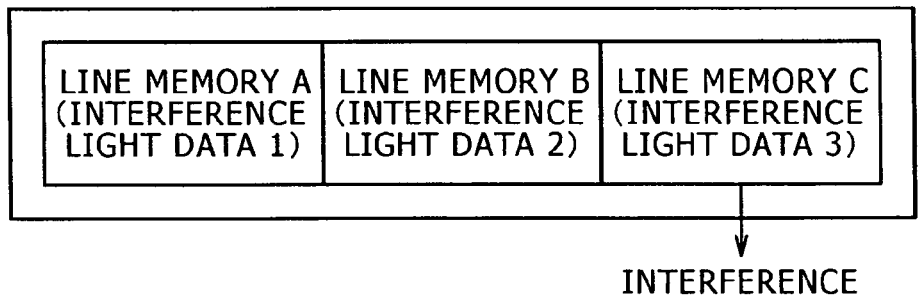

Then assume that interference light data 4 have been inputted as depicted in FIG. 18C. Supposing that no reading of interference light data is being performed from any one of the line memories at the time of the input of the interference light data, a determination is made as to which of the line memories A to C has the oldest interference light data stored therein.

As it is the line memory A that stores the oldest interference light data, the interference light data 4 are written in the line memory A.

When an output pulse is received from the encoder 1506 during the writing of the interference light data 4, reading of interference light data is initiated. Because the line memory A is being written at this time, it is the line memory B or the line memory C that is possibly to be subjected to reading.

Now comparing the interference light data 2 stored in the line memory B with the interference light data 3 stored in the line memory C, the interference light data 3 are newer so that the interference light data 3 stored in the line memory C are read.

Figure 18D:
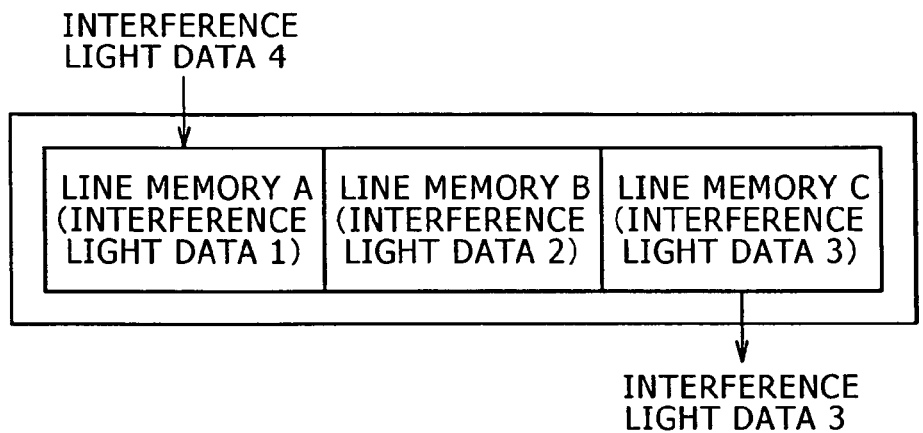

FIG. 18D illustrates a state in which the writing of the interference light data 4 and the reading of the interference light data 3 have been completed. Subsequently, similar processing is repeated.

6.2 Processing for Achieving the Above-Described Signal Processing

Set forth below is a description of processing that is carried out at the line memory unit 1701 to achieve the above-described signal processing. The following description is based on the assumption that the number of lines per rotation is 1,024, though as noted above this number of lines per rotation can be varied.

Figure 19A:
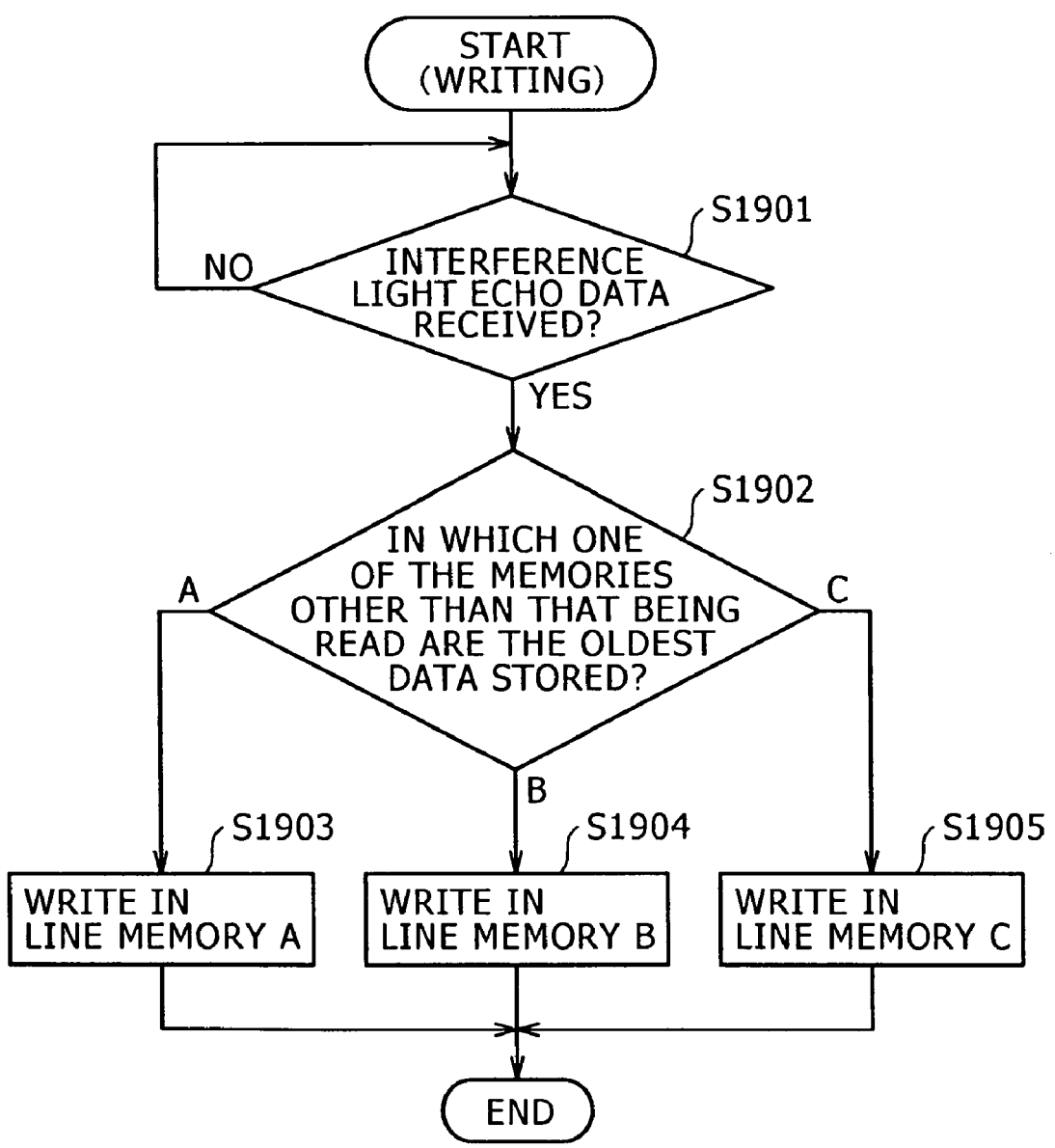
FIG. 19A is a flow chart illustrating the operational aspects of writing processing at the line memory unit.

As shown in FIG. 19A, the writing processing at the line memory unit 1701 begins in step S1901 with a determination of whether or not an input of interference light data in line unit has been made. If the input has not been made, the process remains in a standby condition until the input is made. Once the input has been made, the process advances to step S1902 where the line memory in the line memory unit 1701, other than a line unit being subjected to reading processing, storing the oldest data is determined.

If the particular line memory storing the oldest data is determined to be the line memory A in step S1902, the process then advances to step S1903. If it is determined in step S1902 to be the line memory B, the process advances to step S1904. If it is determined in step S1902 to be the line memory C, the process then advances to step S1905.

In step S1903, the interference light data inputted in step S1901 are written in the line memory A. In step S1904, the interference light data inputted in step S1901 are written in the line memory B. In step S1905, the interference light data inputted in step S1901 are written in the line memory C. The above processing is performed whenever interference light data are inputted.

Figure 19B:
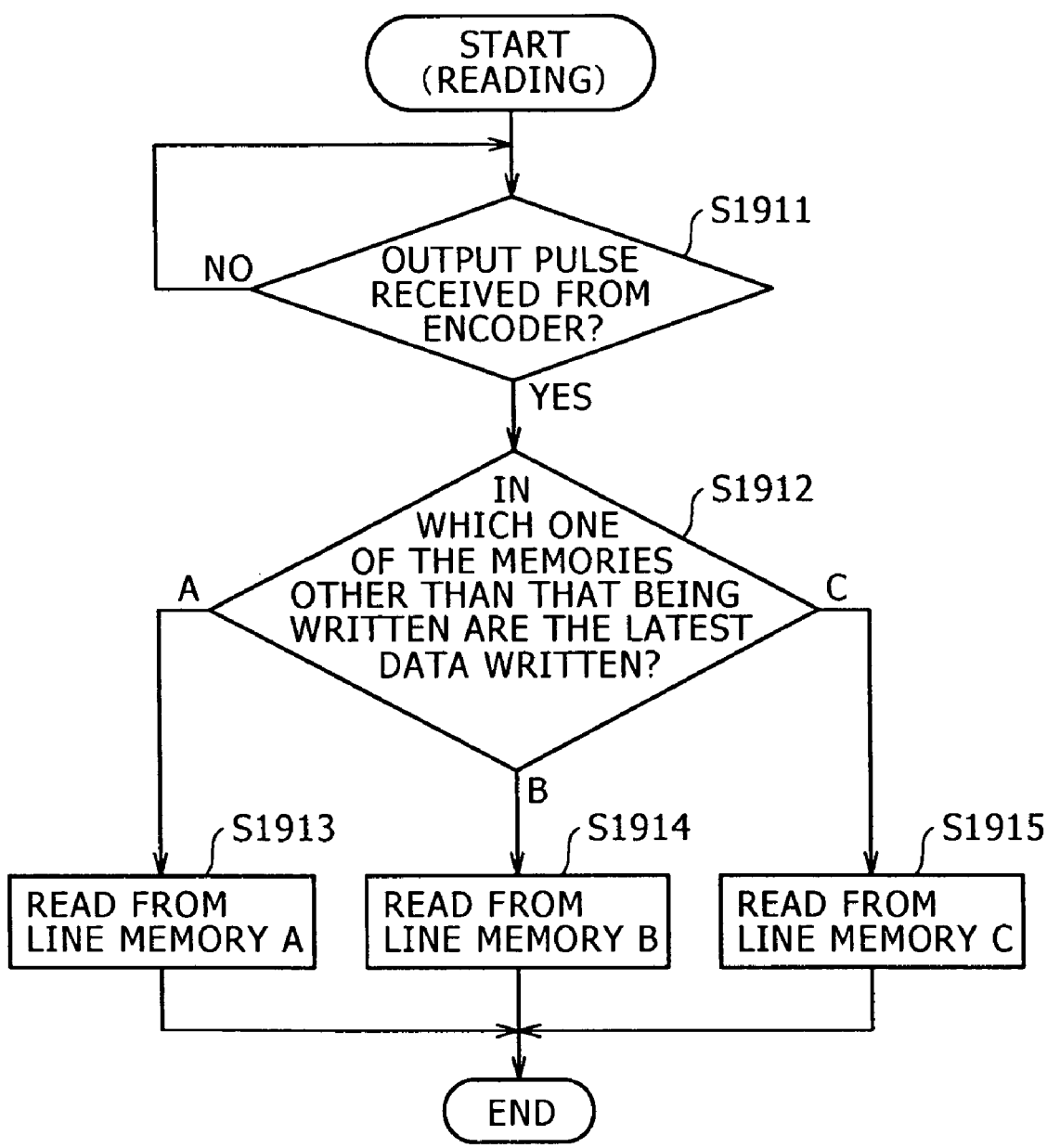
FIG. 19B is a flow chart illustrating operational aspects of reading processing at the line memory unit.

FIG. 19B is a flow chart showing the reading processing at the line memory unit 1701. In step S1911, a determination is made whether or not an output pulse from the encoder 1506 has been received. If it has not been received, the process remains in a standby condition until the output pulse is received. Once the output pulse is received, the process advances to step S1912 where the one of line memories in the line memory unit 1701, other than a line memory being subjected to writing processing, storing the latest (newest) interference light data is determined.

If the particular line memory storing the latest interference light data is determined to be the line memory A in step S1912, the process then advances to step S1913. If it is determined in step S1912 to be the line memory B, the process advances to step S1914. If it is determined in step S1912 to be the line memory C, the process advances to step S1915.

In step S1913, the interference light data stored in the line memory A are read. In step S1914, the interference light data stored in the line memory B are read. In step S1915, the interference light data stored in the line memory C are read. The above processing is performed whenever interference light data are inputted.

6.3 Examples of Writing/Reading Processing at the Line Memory Unit 1701

Examples of the writing/reading processing at the line memory unit 1701 are described below with reference to FIGS. 20A and 20B.

6.3.1 When Not Synchronized (when the Radial Scan Motor is Delayed Relative to the Cycle of Variations in the Optical Path Length of the Reference Mirror)

Figure 20A:
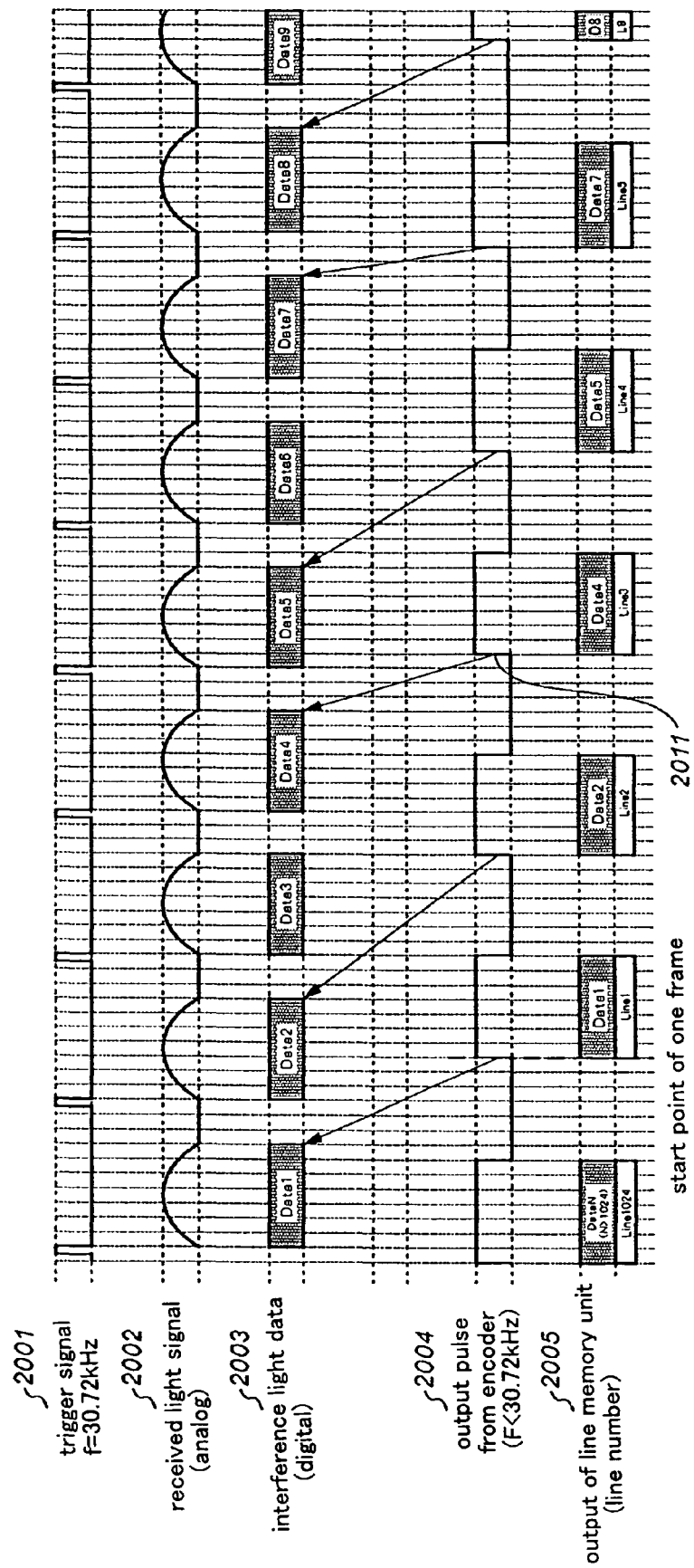
FIG. 20A is a timing chart illustrating when output pulses from an encoder and a movement cycle timing of the optical path of a reference mirror for low-coherence light are out of synchronization.

FIG. 20A is a timing chart illustrating a situation in which the output pulses from the encoder 1506 and the timing of scanning of the optical path length are out of synchronization.

In FIG. 20A, numeral 2001 indicates the timing of trigger signals which control the timing of scanning of the optical path length of the reference mirror. Numeral 2002 designates signals received as reflected light from a surrounding biotissue of a body cavity in response to low-coherence light scanning the optical path length based on the trigger signals 2001.

FIG. 20A shows that the output pulses from the encoder 1506 are delayed relative to the timing of production cycle of interference light data (scanning of the optical path length).

Specifically, FIG. 20A shows a state in which, because the output pulses from the encoder 1506 are delayed relative to the production cycle timing of interference light data, the reading of Data 4 is performed without effecting the reading of Data 3.

In other words, despite the production of Data 3 as interference light data (2003), Data 4 are produced and stored in the lime memory unit 1701 before Data 3 are read. At the point in time (timing 2011) that an output pulse from the encoder 1506 has been received, the latest interference light data are, therefore, determined to be Data 4 instead of Data 3. As a result, Data 3 are not read, but Data 4 are read.

It is to be noted that Data 3 will not be used for the construction of a tomographic image because they will be overwritten by interference light data to be produced subsequently.

6.3.2 When Not Synchronized (when the Radial Scan Motor is Advanced Relative to the Cycle of Scanning of the Optical Path Length of the Reference Mirror)

Figure 20B:
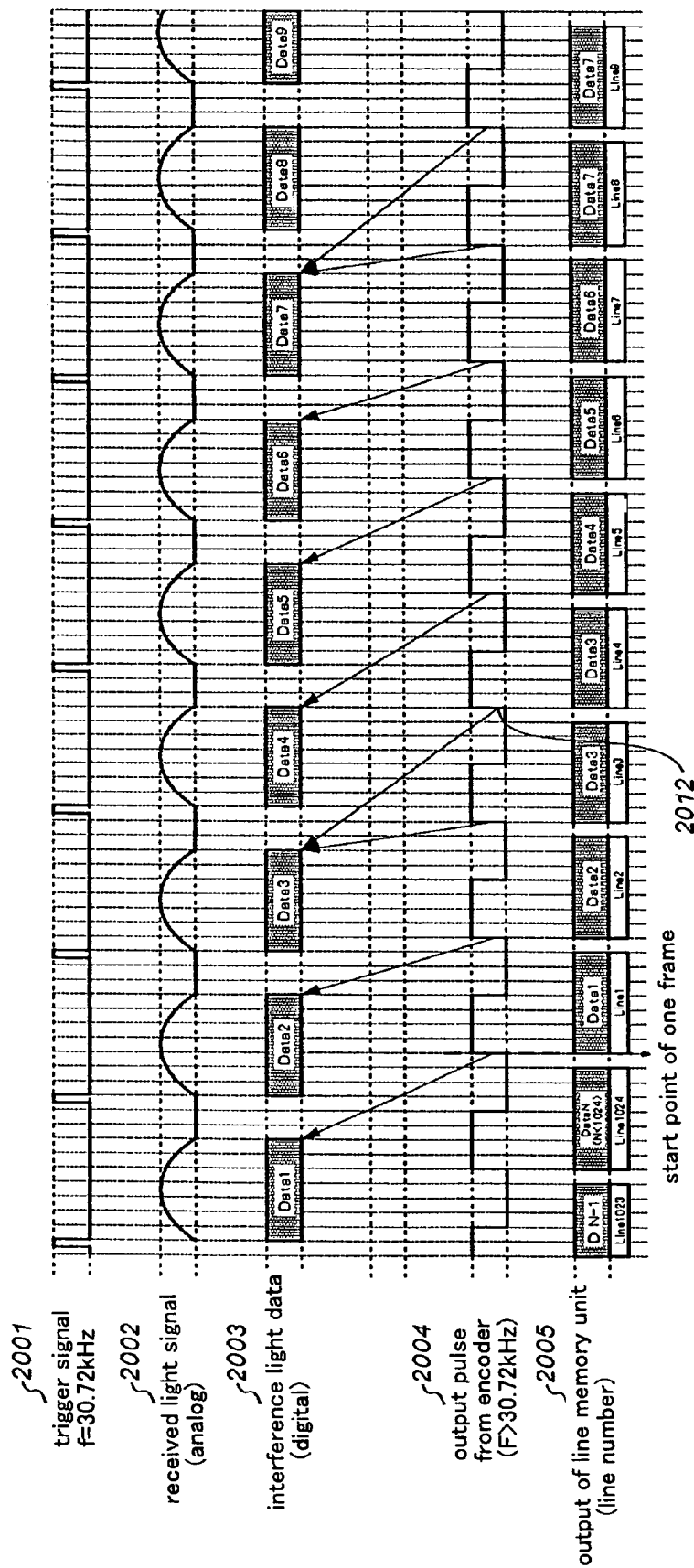
FIG. 20B is a timing chart illustrating when output pulses from an encoder and a movement cycle timing of the optical path of a reference mirror for low-coherence light are also out of synchronization.

FIG. 20B is a timing chart illustrating a situation in which the output pulses from the encoder 1506 and the timing of scanning of the optical path length are out of synchronization. FIG. 20B shows that the output pulses from the encoder 1506 are advanced relative to the production cycles of interference light data for an advance of the radial scan motor.

Specifically, FIG. 20B shows a state in which, because the output pulses from the encoder 1506 are advanced relative to the production cycles of interference light data, the production of interference light data as Data 4 has not been completed at the timing that Data 4 are supposed to be read, and therefore, the reading of Data 3 has been performed again.

In other words, at a time (2012) when an output pulse from the encoder 1506 is received, the latest interference light data are determined to be Data 3 so that the reading of Data 3 is performed again.

As is evident from the above description, the OCT imaging system according to this embodiment makes it possible to perform appropriate reading of interference light data in accordance with the rotation cycle of the probe in radial scanning even when synchronization is not achieved between the rotation cycle of the probe in the radial scanning and the production cycle of interference light data from the probe.

As a result, it is possible to reduce or eliminate difficulties encountered in other systems mentioned above in which a tomographic image may be displayed blurred in the circumferential direction or may be displayed while slowly turning.

Third Embodiment

The second embodiment described above applies subject matter disclosed herein to an OCT imaging system. However, the subject matter at issue here is not specifically limited to OCT imaging systems, but can also be applied to OCT imaging systems making use of a wavelength swept light source. The following description describes application of the disclosed subject matter to an OCT imaging system making use of a wavelength swept light source.

1. Measurement Principle of OCT Imaging System Making Use of a Wavelength Swept Light Source Initially, a brief description is set forth of the measurement principle of the OCT imaging system making use of a wavelength swept light source. This OCT imaging system and the OCT imaging system described above as the second embodiment are basically the same in terms of the measurement principle as generally illustrated in FIGS. 13 and 14. The following description primarily discusses differences of this version of the OCT imaging system relative to the OCT imaging system described above as the second embodiment.

It is the optical source that is different in measurement principle from the OCT imaging system described above as the second embodiment. First, these OCT imaging systems are thus different in coherence length. More specifically, a light source capable of emitting low-coherence light of from 10 μm to 20 μm or so in coherence length is used as the light source in the OCT imaging system described above as the second embodiment. On the other hand, a light source capable of emitting coherence light of from 4 mm to 10 mm or so in coherence length is used as a light source in the OCT imaging system making use of a wavelength swept light source.

As a reason for the above-mentioned difference, the range of the examinable range in the direction of the depth of a biotissue is dependent on the movable range of the reference mirror in the OCT imaging system described above as the second embodiment, but is dependent on the coherence length in the OCT imaging system making use of a wavelength swept light source. To encompass the entire range in the direction of the depth of a biotissue such as a blood vessel, an optical source having a relatively long coherence length is used in the OCT imaging system making use of a wavelength swept light source.

Another difference in the light sources resides in that in the case of the OCT imaging system making use of a wavelength swept light source, light beams having different wavelengths are continuously irradiated.

In the OCT imaging system according to the second embodiment described above, the extraction of reflected light from individual points in the direction of the depth of the biotissue is achieved by movements of the reference mirror, and the resolution in the direction of the depth of the measurement target is dependent on the coherence length of irradiated light.

In the OCT imaging system making use of a wavelength swept light source, on the other hand, light is irradiated while continuously varying its wavelength and the intensities of reflected light from individual points in the direction of the depth of the biotissue are determined based on differences in the frequency component of interference light.

Taking the frequency (the inverse of the wavelength) of scanning light as a time function represented by Equation 1 below, the intensity of interference light can generally be expressed by a time function represented by Equation 2.

$$f(t)=f_\alpha+\Delta ft \qquad \text{(Equation 1)}$$

$$I(t)=A+B\cos(C\Delta x(f_\alpha+\Delta ft)) \qquad \text{(Equation 2)}$$

where $\Delta x$: optical path difference between the reference light and the target light, $\Delta f$: the rate of a change in frequency in unit time, and A,B,C: constants.

As indicated by Equation 2, the frequency component in the time-dependent change in the intensity I(t) of reference light is expressed by the optical path difference $\Delta x$ and the rate $\Delta f$ of a change in frequency by frequency scanning. Accordingly, the intensity of interference light for each optical path difference can be determined provided that the frequency component of the interference light is known, and signals for one line can be obtained by a single cycle of wavelength sweep.

As a consequence, the time required for acquiring signals for one line can be shortened, and further the imaging depth can be made greater.

Figure 21:
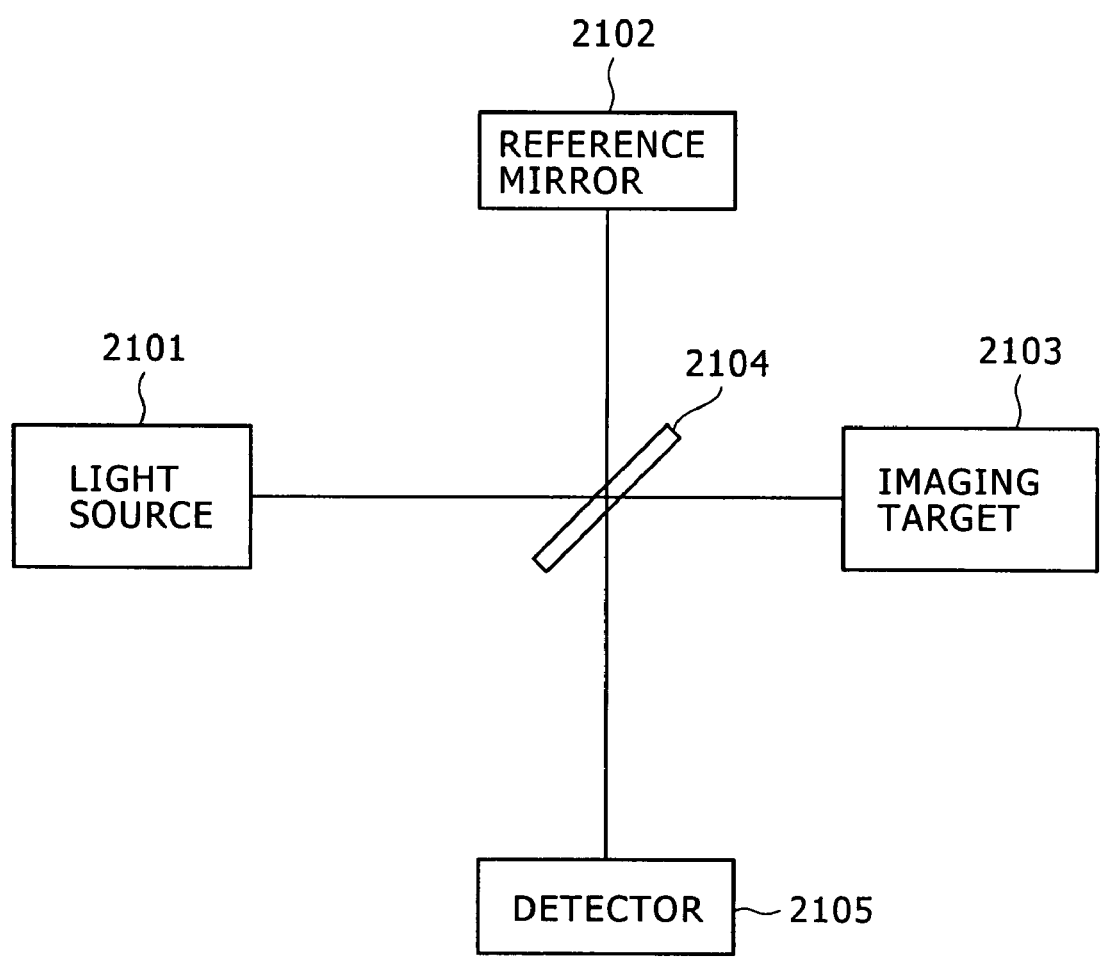
FIG. 21 is a block diagram illustrating the basic principle of an OCT imaging system according to a third embodiment, which makes use of a wavelength swept light source.

An example of the basic principle of an OCT imaging system making use of a wavelength swept light source is shown in FIG. 21 which depicts the light source 2101 as a swept laser.

Light beams, which have been successively outputted from the light source 2101 and have different wavelengths, are each split at a beam splitter 2104, and the thus-split light beams then travel toward a reference mirror 2102 and an imaging target 2103, respectively. At this time, reflected light which is returning from the side of the imaging target 2103 includes light reflected on the surface of the imaging target, light reflected at shallow points in the imaging target, and light reflected at deep points in the imaging target.

By subjecting observed interference light to frequency decomposition at a detector 2105 as mentioned above, information on a structure at a particular position in the direction of the depth of the measuring target can be visualized. As a result, data for one line can be obtained by a single cycle of wavelength sweep, thereby making it possible to construct a tomographic image.

As the light outputted from the light source 2101 is of from 4 mm to 6 mm or so in coherence length, it is possible to encompass the entire examination range in the direction of the depth of the imaging target. It is, therefore, unnecessary to move the reference mirror, so that the reference mirror 2102 is arranged fixedly at a constant distance. Moreover the reference mirror is not indispensable in this embodiment as a turned optical fiber, which can return back the light, may be set at the distal end of the reference optical path instead of the reference mirror Because it is unnecessary to mechanically move the reference mirror as mentioned above, the OCT imaging system making use of a wavelength swept light source, in comparison with the OCT imaging system according to the previously described second embodiment, requires a shorter time for acquiring signals for one line and can raise the frame rate. As opposed to a maximum frame rate of 15 fr/s (i.e., frames/second) in the OCT imaging system according to the second embodiment, the frame rate of the OCT imaging system making use of a wavelength swept light source is as high as from 30 to 200 fr/s or so.

In the case of an OCT imaging system irrespective of whether or not it makes use of a wavelength swept light source, blood is supposed to be eliminated upon diagnosis so that absorption of light by blood cell components can be avoided to acquire good images. A low frame rate, therefore, requires the elimination of blood for a longer time. This, however, leads to problems from the clinical standpoint. In the case of an OCT imaging system making use of a wavelength swept light source, images can be acquired over 30 mm or longer in the axial direction of a blood vessel by elimination of blood for several seconds, thereby reducing such clinical problems.

Figure 22:
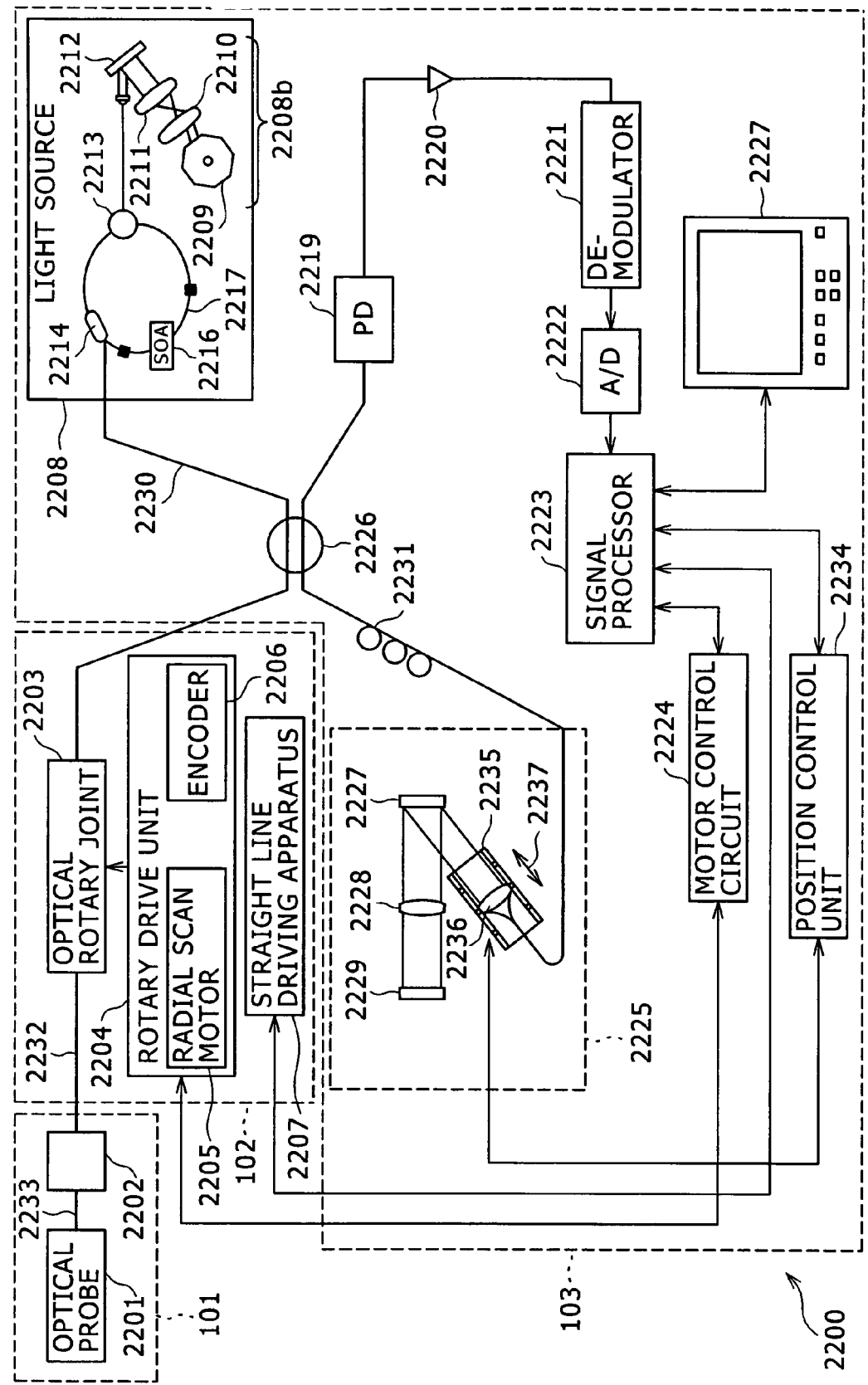
FIG. 22 is a block diagram illustrating functional aspects of the OCT imaging system making use of a wavelength swept light source.

2. Aspects and Features of OCT Imaging System Making Use of a Wavelength Swept Light Source Features and aspects of the OCT imaging system 2200 making use of a wavelength swept light source are schematically shown in FIG. 22. The description which follows primarily describes differences in the OCT imaging system 2200 making use of a wavelength swept light source relative to the OCT imaging system described above as the second embodiment with reference to FIG. 15.

The OCT imaging system 2200 making use of a wavelength swept light source includes a light source 2208. In the disclosed embodiment, a swept laser is used as the light source 2208. This swept laser 2208 is a kind of extended-cavity laser which includes an optical fiber 2217 and a polygon scanning filter 2208*b*. The optical fiber 2217 is connected in the form of a ring with a semiconductor optical amplifier (SOA) 2216.

Light outputted from the SOA 2216 advances through the optical fiber 2217 and enters the polygon scanning filter 2208*b*. Subsequent to wavelength selection through the polygon scanning filter 2298*b*, the resulting light is amplified at the SOA 2216 and is finally outputted from a coupler 2214.

The polygon scanning filter 2208*b* selects a wavelength by a combination of a diffraction grating 2212, which separates light into a spectrum, and a polygon mirror 2209. The light, which has been separated into the spectrum by the diffraction grating 2212, is condensed on a facet of the polygon mirror 2209 by two lenses (2210, 2211). As a result, only light of a wavelength crossing at a right angle with the polygon mirror 2209 returns on the same light path and is outputted from the polygon scanning filter 2208*b*. By rotating the mirror, time sweeping of wavelengths is performed.

As an example of the polygon mirror 2209, a 32-faced polygonal mirror can be used, and its rotational speed can be 50,000 rpm or so. By the unique wavelength sweep system making the combined use of the polygon mirror 2209 and the diffraction grating 2212, high-speed and high-output wavelength sweep is feasible.

The light of the swept laser 2208, which has been outputted from the coupler 2214, impinges on the proximal end of a first single mode fiber 2230 and is transmitted toward its distal end face. At an optical coupler 2226 arranged midway along the first single mode fiber 2230, the first single mode fiber 2230 is optically coupled with a second single mode fiber 2231. Therefore, the light transmitted through the first single mode fiber 2230 is split into two by the optical coupler 2226 and the resulting two beams of light are transmitted further.

On the more distal end side of the first single mode fiber 2230 than the optical coupler 2226, an optical rotary joint 2203 is arranged to connect a non-rotatable block and a rotatable block with each other such that light can be transmitted.

Further, an optical-probe connector 2202 is detachably connected to the distal end of a third single mode fiber 2232 in the optical rotary joint 2203. Via the connector 2202, the light from the light source 2208 is transmitted to a fourth single mode fiber 2223 which is inserted in an optical probe 2201 and is rotationally drivable.

The transmitted light is irradiated from a distal end side of the optical probe 2201 toward a surrounding biotissue of a body cavity while performing radial scanning. A portion of reflected light scattered on a surface or interior of the biotissue is collected by the optical probe 2201, and returns toward the first single mode fiber 2230 through the reverse optical path. A portion of the thus-collected, reflected light is transferred by the optical coupler 2226 to the second single mode fiber 2231 and is introduced into a photodetector (for example, photodiode 2219) from an end of the second single mode fiber 2231. It is to be noted that the rotatable block side of the optical rotary joint 2203 is rotationally driven by a radial scan motor 2205 of a rotary drive unit 2204. Further, rotation angles of the radial scan motor 2205 are detected by an encoder 2206. The optical rotary joint 2203 is provided with a linear drive unit 2207 which, based on an instruction from a signal processor 2223, controls movement of the catheter section 101 in the direction of its insertion.

On the more distal end side of the second single mode fiber 2231 than the optical coupler 2226, an optical path length (OPL) varying mechanism 2225 is arranged to finely adjust the optical path length of reference light.

This OPL varying mechanism 2225 is provided with a an OPL varying means for varying the optical path length by a length equivalent to a variation in the length of a new optical probe to absorb the variation when the new optical probe is used as a replacement.

The second single mode fiber 2231 and a collimator lens 2236 are mounted on a single axis stage 2235 movable in the direction of an optical axis of the collimator lens 2236.

More specifically, the single axis stage 2235 forms the OPL varying means having a variable OPL range just enough to absorb a variation in the optical path length of a new optical probe when the optical probe 2201 is replaced by the new optical probe. In addition, the single axis stage 2235 is also equipped with a function as an adjustment means for adjusting an offset. Even when the distal end of the optical probe 2201 is not in close contact with a surface of the biotissue, for example, the optical probe can still be set in such a state as interfering from a position on the surface of the biotissue by slightly varying the optical path length with the single axis stage 2235.

The light finely adjusted in optical path length by the OPL varying mechanism 2225 is combined with the light, which has escaped from the side of the first single mode fiber 2230, at the optical coupler 2226 arranged midway along the second single mode fiber 2231, and the combined light is received at the photodiode 2219.

The light received at the photodiode 2219 is photoelectrically converted, amplified by an amplifier 2220, and then inputted into a demodulator 2221. At the demodulator 2221, demodulation processing is performed to extract only the signal portion of the interfered light, and the output of the demodulator 2221 is inputted into an A/D converter 2222.

At the A/D converter 2222, interference light signals are sampled at 180 MHz as much as for 2,048 points to produce digital data (interference data) for one line. It is to be noted that the setting of the sampling frequency at 180 MHz is attributed to the premise that approximately 90% of the cycle of wavelength sweep (12.5 μsec) be extracted as digital data at 2,048 points when the wavelength sweep repetition frequency is set at 40 kHz. The sampling frequency should be understood, therefore, not to be limited specifically to the above-described value.

The interference light data in line unit, which have been produced at the A/D converter 2222, are inputted into a signal processor 2223. At this signal processor 2223, the interference light data are frequency-resolved by FFT (Fast Fourier Transform) to produce data in the direction of the depth. These data are then coordinate-transformed to construct tomographic images at respective positions in the blood vessel. The tomographic images are then outputted at a predetermined frame rate to an LCD monitor 2227.

It is to be noted that the signal processor 2223 is connected with a position control unit 2234. The signal processor 2223 performs control of the position of the single axis stage 2235 via the position control unit 2234. In addition, the signal processor 2223 is also connected with a motor control circuit 2224 to control rotational drive by the radial scan motor 2205.

3. Construction of Catheter Section

The overall construction of the catheter section 101 and the construction of the distal end portion of the catheter are similar to those of the catheter and catheter section in the OCT imaging device described above as the second embodiment with reference to FIG. 16. Thus, a detailed description of the features of the catheter section is not repeated.

4. Features of Signal Processor

Figure 23:
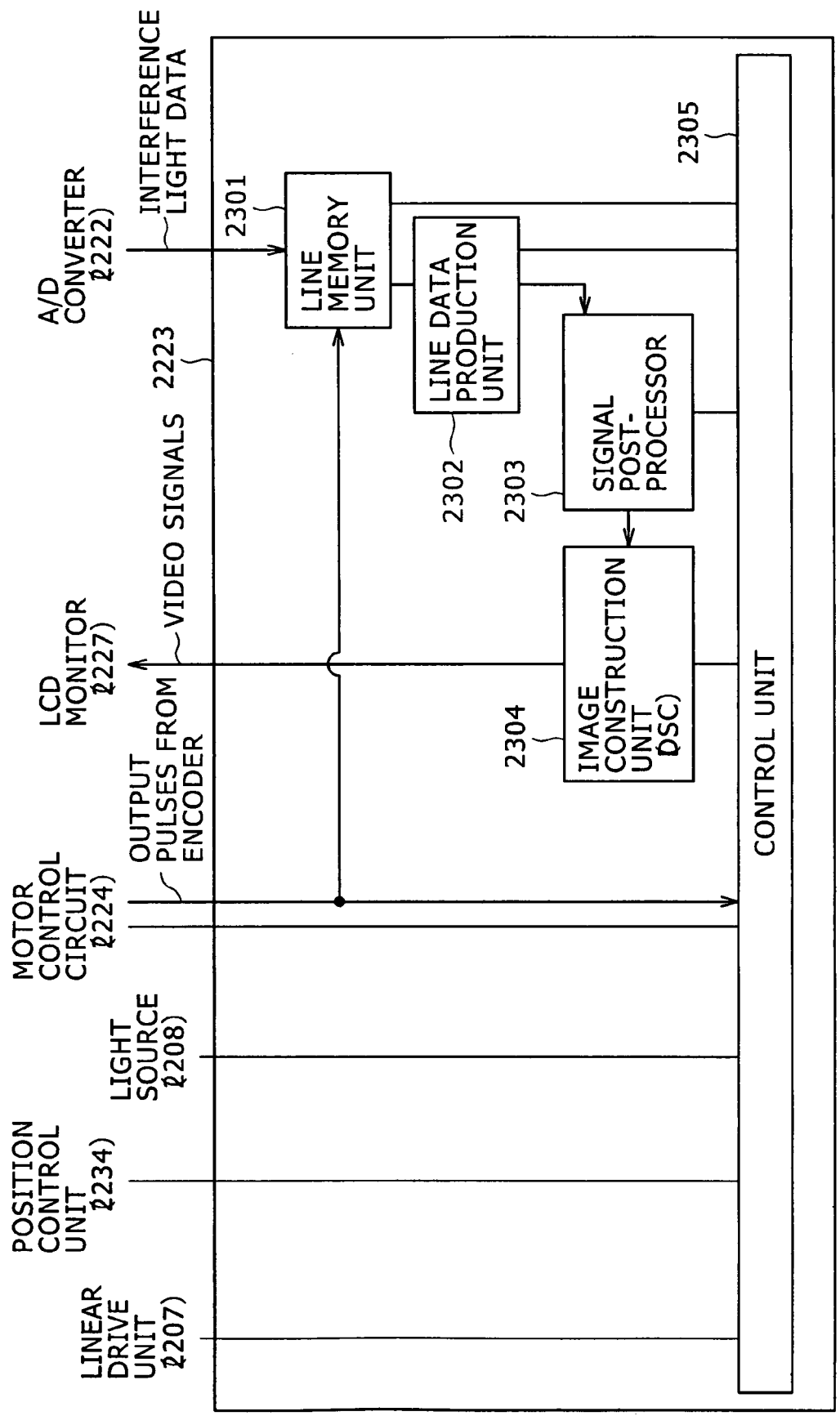
FIG. 23 is a block diagram depicting operational aspects of a signal processing unit in the OCT imaging system making use of a wavelength swept light source.

Features of the signal processor 2223 in the OCT imaging system 2200 making use of a wavelength swept light source are schematically illustrated in FIG. 23. The signal processor 2223 includes a control unit 2305 which systematically controls the OCT imaging system 2200 making use of a wavelength swept light source in its entirety. The signal processor 2223 also includes line memory unit 2301. At the line memory unit 2301, interference light data transmitted from the photodiode 2210 via the demodulator 2221 and A/D converter 2222 are successively received in cycle units of wavelength sweep, and are temporarily held.

The interference light data temporarily held in the line memory unit 2301 are read in accordance with output pulses from the encoder 2206 as needed (based on instructions from the control unit 2305), and subsequent to their frequency resolution into data in the direction of the depth by FFT, are fed to a signal post-processor 2303 by a line data construction unit 2302. Additional details about the line memory unit 2301, the writing operations to the line memory unit 2301 and the reading operations from the line memory unit 2301 will be described below.

The signal post-processor 2303 performs processing such as frame correlation, gamma correction, contrast adjustment and sharpness filtering on the interference data read from the line data construction unit 2302, and outputs the resulting data to an image construction unit 2304.

At the image construction unit 2304, streams of interference light data in cycle units of wavelength sweep of interference light (line units) are converted into video signals having a predetermined gray scale. Based on the video signals, tomographic images to be displayed on the LCD monitor 2227 are constructed.

5. Processing at the Line Memory Unit 2301

5.1 Features of the Line Memory Unit 2301 and Processing at the Line Memory Unit 2301

FIGS. 24A-24D illustrate features associated with the line memory unit 2301 in the OCT imaging system 2200 according to the third embodiment and the processing that occurs at the line memory unit 2301. The line memory unit 2301 is composed of line memories (2401, 2402, 2403) for three lines. Interference light data are inputted in wavelength sweep cycle units (line units) to the line memory unit 2301. The inputted interference light data are written in the line memories in synchronization with the timing of wavelength sweep of interference light.

Here, each writing is performed to the one of the line memories, other than a line memory being read, storing oldest interference light data. At this time, the oldest interference light data which have already been written are deleted.

On the other hand, the reading of interference light data from each line memory is performed in synchronization with a corresponding output pulse from the encoder 2206. The reading is performed from the one of the line memories, other than the line memory being read, storing the latest (newest) interference light data.

Figure 24A:
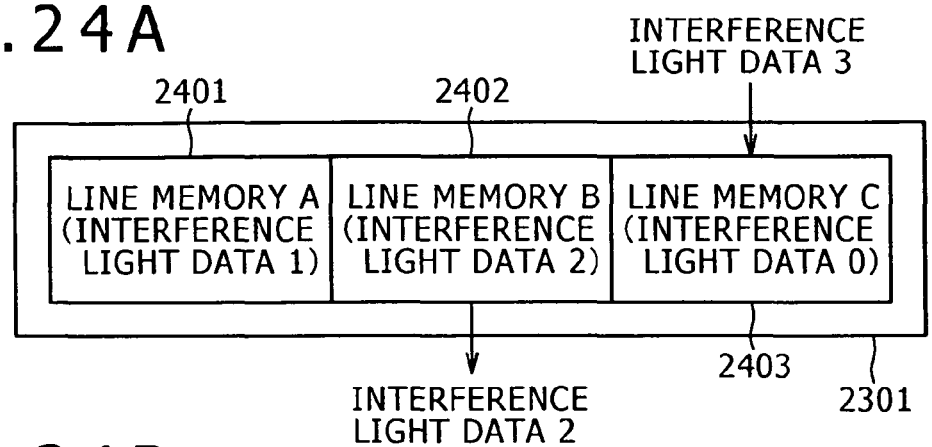
FIGS. 24A-24D are schematic illustrations of aspects of a line memory unit in the OCT imaging system making use of a wavelength swept light source and the outline of processing at the line memory unit.

An example is described with reference to FIGS. 24A-24D. FIG. 24A illustrates a state in which interference light data 1 are stored in the line memory A(2401), interference light data 2 are stored in the line memory B(2402), and interference light data 0 are stored in the line memory C(2403).

Now assume that interference light data 3 have been inputted. Supposing that no reading of interference light data is being performed from any one of the line memories at the time point of the input of the interference light data 3, a determination is made as to which one of the line memories A(2401) to C(2403) contains the oldest interference light data.

Now assume that these interference light data become older in the order of the interference light data 2→the interference light data 1→the interference light data 0 (oldest). Accordingly, it is the line memory C(2403) that stores the oldest interference light data, and the interference light data 3 are hence written in the line memory C(2403). The writing of interference light data in the line memory can be controlled by a writing control unit forming a part of the control unit.

When an output pulse is received from the encoder 2206 during the writing of the interference light data 3, reading of interference light data is initiated. Because the line memory C(2403) is being written at this time, it is either the line memory A(2401) or the line memory B(2402) that is possibly to be subjected to reading.

Now comparing the interference light data 1 stored in the line memory A(2401) with the interference light data 2 stored in the line memory B(2402), the interference light data 2 are newer and so the interference light data 2 stored in the line memory B(2402) are read. The reading of the interference light data in the line memory can be controlled by a reading control unit forming a part of the control unit.

Figure 24B:
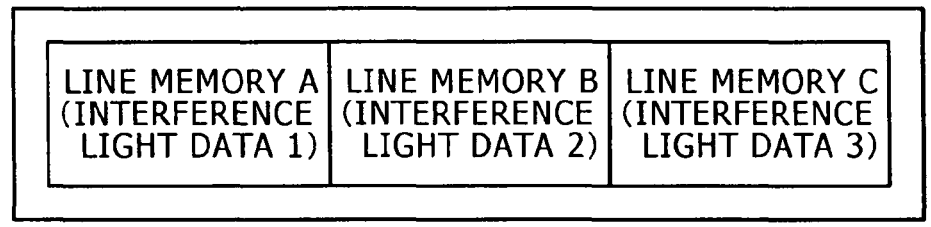

FIG. 24B illustrates a state in which the writing of the interference light data 3 and the reading of the interference light data 2 have been completed.

Figure 24C:
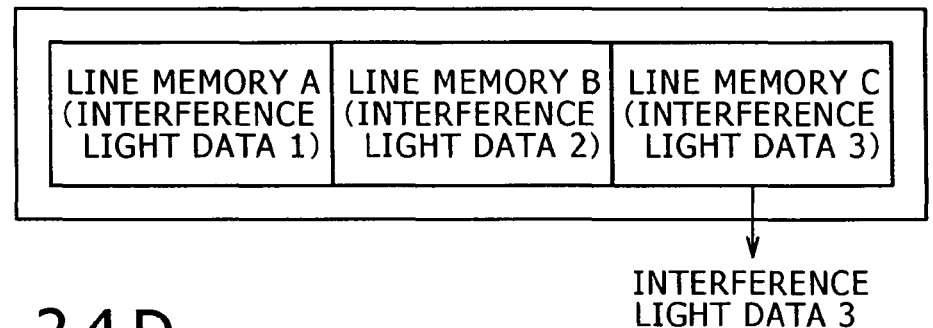

Then assume that interference light data 4 have been inputted as depicted in FIG. 24C. Supposing that no reading of interference light data is being performed from any one of the line memories at the point in time of the input of the interference light data, a determination is made as to the one of the line memories A to C in which is stored the oldest interference light data.

As it is the line memory A that stores the oldest interference light data, the interference light data 4 are written in the line memory A.

When an output pulse is received from the encoder 2206 during the writing of the interference light data 4, reading of interference light data is initiated. Because the line memory A is being written at this time, it is either the line memory B or the line memory C that is possibly to be subjected to reading.

Now comparing the interference light data 2 stored in the line memory B with the interference light data 3 stored in the line memory C, the interference light data 3 are newer and so the interference light data 3 stored in the line memory C are read.

Figure 24D:
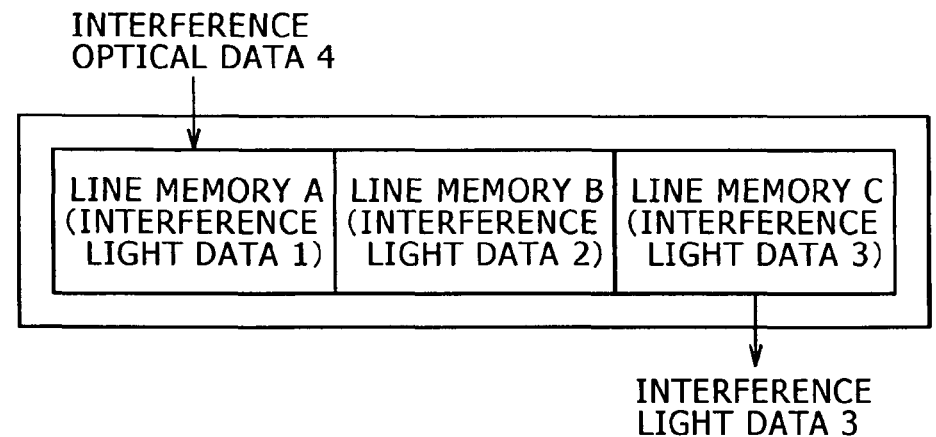

FIG. 24D illustrates a state in which the writing of the interference light data 4 and the reading of the interference light data 3 have been completed. Subsequently, similar processing is repeated.

5.2 Processing for Achieving the Above-Described Signal Processing

Set forth below is a description of the processing at the line memory unit 2301 to achieve the above-described signal processing. It is to be noted that the description will hereinafter be made under the assumption that the number of lines per rotation is 1,024, though this can be varied.

Figure 25A:
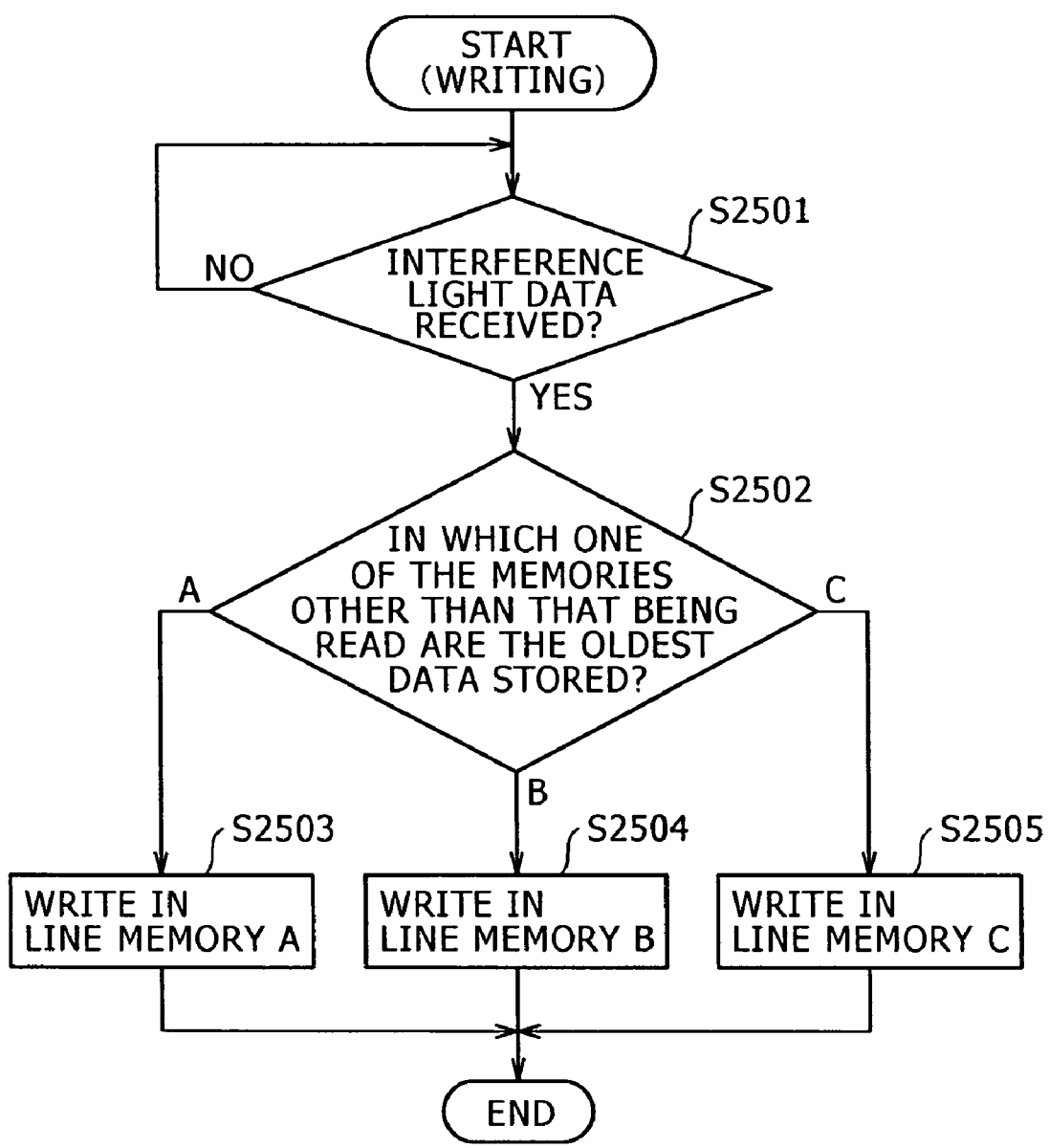
FIG. 25A is a flow chart showing aspects of the writing processing at the line memory unit.

The writing processing at the line memory unit 2301 is carried out as shown in FIG. 25A. Initially, in step S2501, a determination is made as to whether or not an input of interference light data in line unit has been made. If the input has not been made, the process remains in standby. One the input is made, the process advances to step S2502 in which it is determined which of the line memories in the line memory unit 2301, other than a line unit being subjected to reading processing, is the line memory storing the oldest interference light data.

If the particular one line memory storing the oldest interference light data is determined to be the line memory A in step S2502, the process advances to step S2503. If it is determined in step S2502 to be the line memory B, the process advances to step S2504. If it is determined in step S2502 to be the line memory C, the process advances to step S2505.

In step S2503, the interference light data inputted in step S2501 are written in the line memory A. In step S2504, the interference light data inputted in step S2501 are written in the line memory B. In step S2505, the interference light data inputted in step S2501 are written in the line memory C. The above processing is performed whenever interference light data are inputted.

Figure 25B:
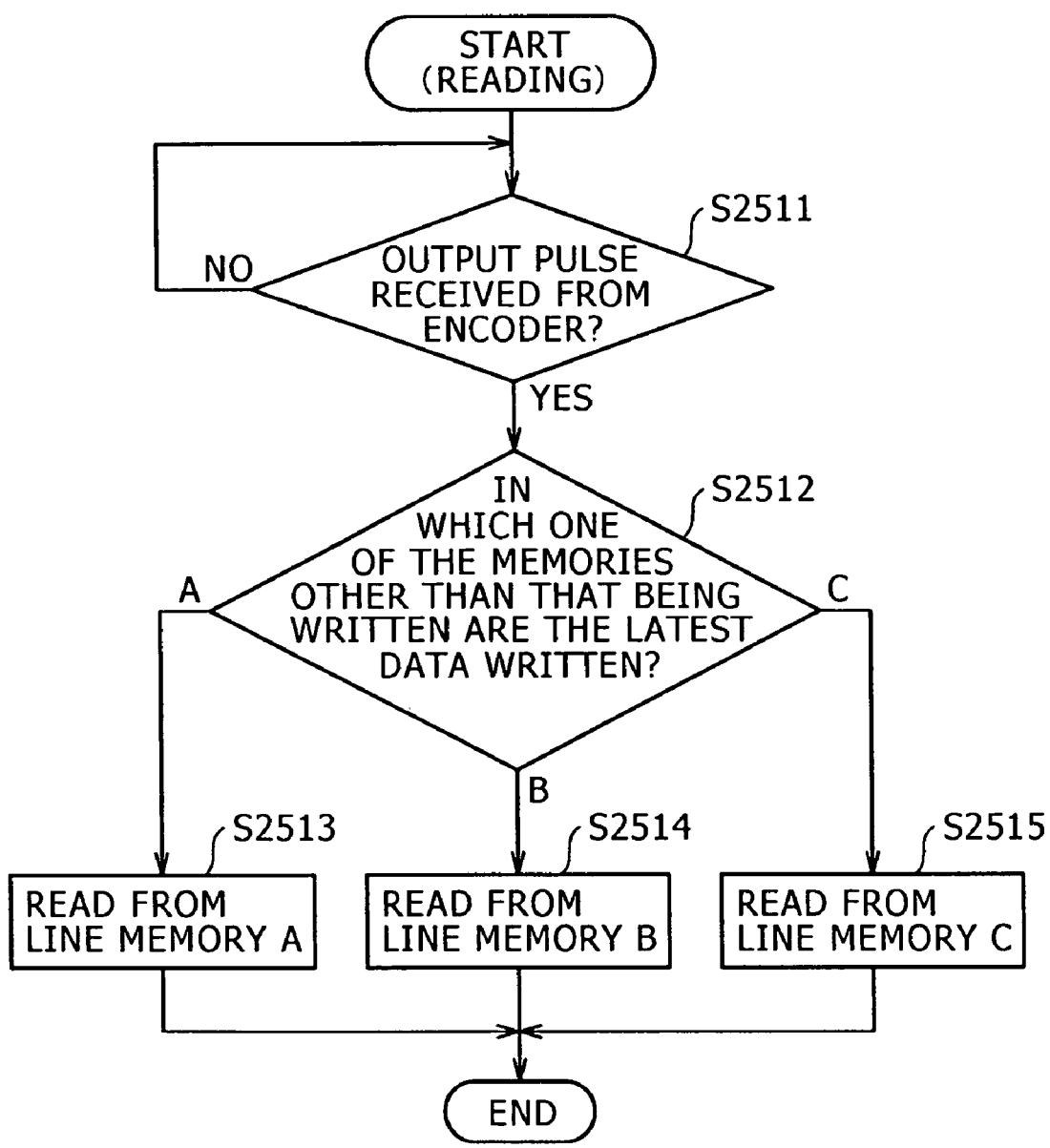
FIG. 25B is a flow chart showing aspects of the reading processing at the line memory unit.

The reading processing at the line memory unit 2301 is shown by the flow chart in FIG. 25B. In step S2511, a determination is made as to whether or not an output pulse from the encoder 2206 has been received. If it has not been received, the process remains in standby. Once the output pulse is received, the process advances to step S2512, in which the one of the line memories in the line memory unit 2301, other than a line memory being subjected to writing processing, storing the latest (newest) interference light data is determined.

If the particular one line memory is determined to be the line memory A in step S2512, the process advances to step S2513. If it is determined in step S2512 to be the line memory B, the process advances to step S2514. If it is determined in step S2512 to be the line memory C, the process advances to step S2515.

In step S2513, the interference light data stored in the line memory A are read. In step S2514, the interference light data stored in the line memory B are read. In step S2515, the interference light data stored in the line memory C are read. The above processing is performed whenever interference light data are inputted.

5.3 Examples of Writing/Reading Processing at the Line Memory Unit 2301

Examples of the writing/reading processing at the line memory unit 2301 are described below with reference to FIGS. 26A and 26B.

5.3.1 When Not Synchronized (when the Radial Scan Motor is Delayed Relative to the Cycle of Wavelength Sweep)

Figure 26A:
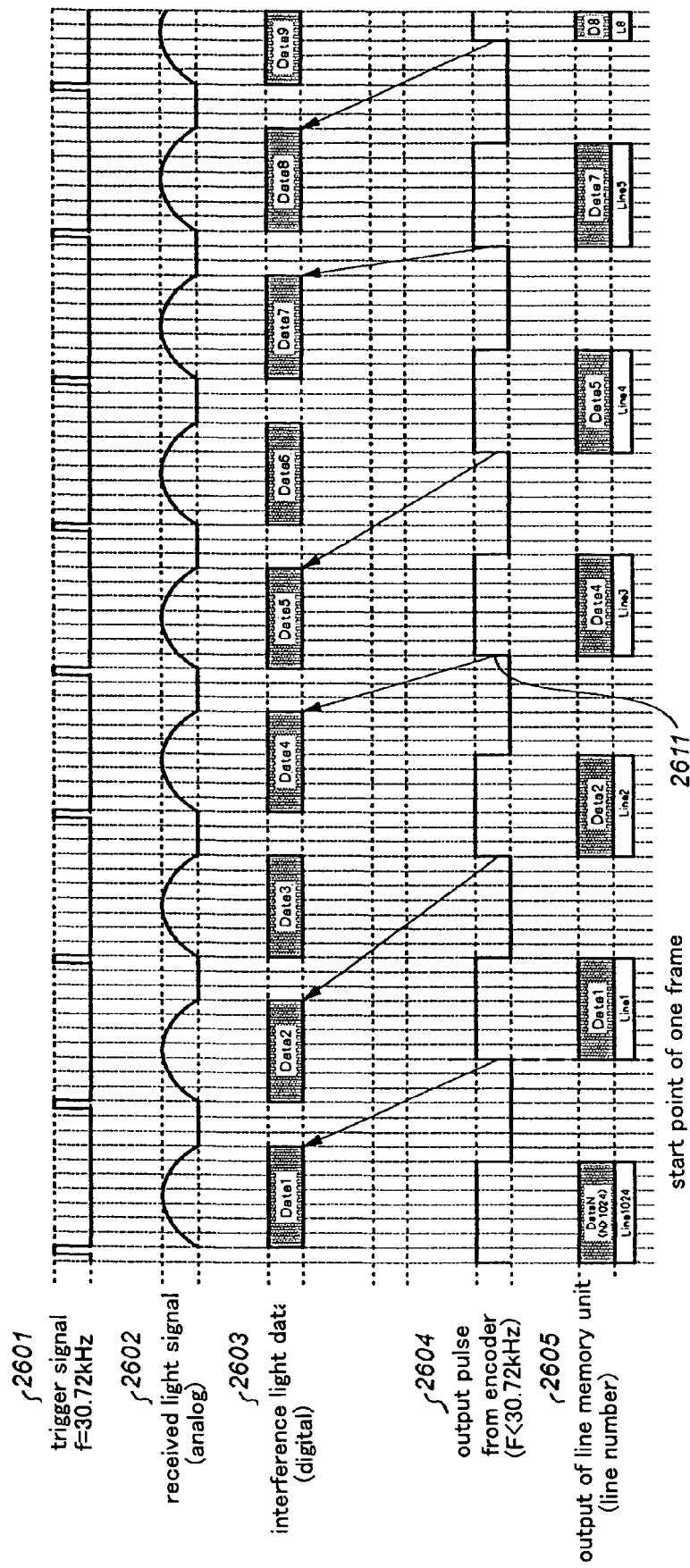
FIG. 26A is a timing chart illustrating when output pulses from an encoder and a timing of wavelength sweep of irradiation light are out of synchronization.

FIG. 26A is a timing chart illustrating a situation in which the output pulses from the encoder 2206 and the timing of wavelength sweep cycle are out of synchronization. In this figure, numeral 2601 indicates the timing of trigger signals which control the timing of wavelength sweep. Numeral 2602 designates the timing of reception of reflected light from a surrounding biotissue of a body cavity in response to light subjected to wavelength sweep on the basis of the trigger signals 2601.

FIG. 26A shows that the output pulses from the encoder 2206 are delayed relative to the timing of production of interference light data for a delay of the radial scan motor. Specifically, FIG. 26A shows a state that, because the output pulses from the encoder 2206 are delayed relative to the production timing of interference light data, the reading of Data 4 is performed without effecting the reading of Data 3.

In other words, despite the production of Data 3 as interference light data (2603), Data 4 are produced and stored in the lime memory unit 2301 before Data 3 are read. At the point in time (timing 2611) when an output pulse from the encoder 2206 has been received, the latest interference light data are, therefore, determined to be Data 4 instead of Data 3. As a result, Data 3 are not read, but rather Data 4 are read.

It is to be noted that Data 3 will not be used for the construction of a tomographic image because they will be overwritten by interference light data to be produced subsequently.

5.3.2 When Not Synchronized (when the Radial Scan Motor is Advanced Relative to the Cycle of Wavelength Sweep)

Figure 26B:
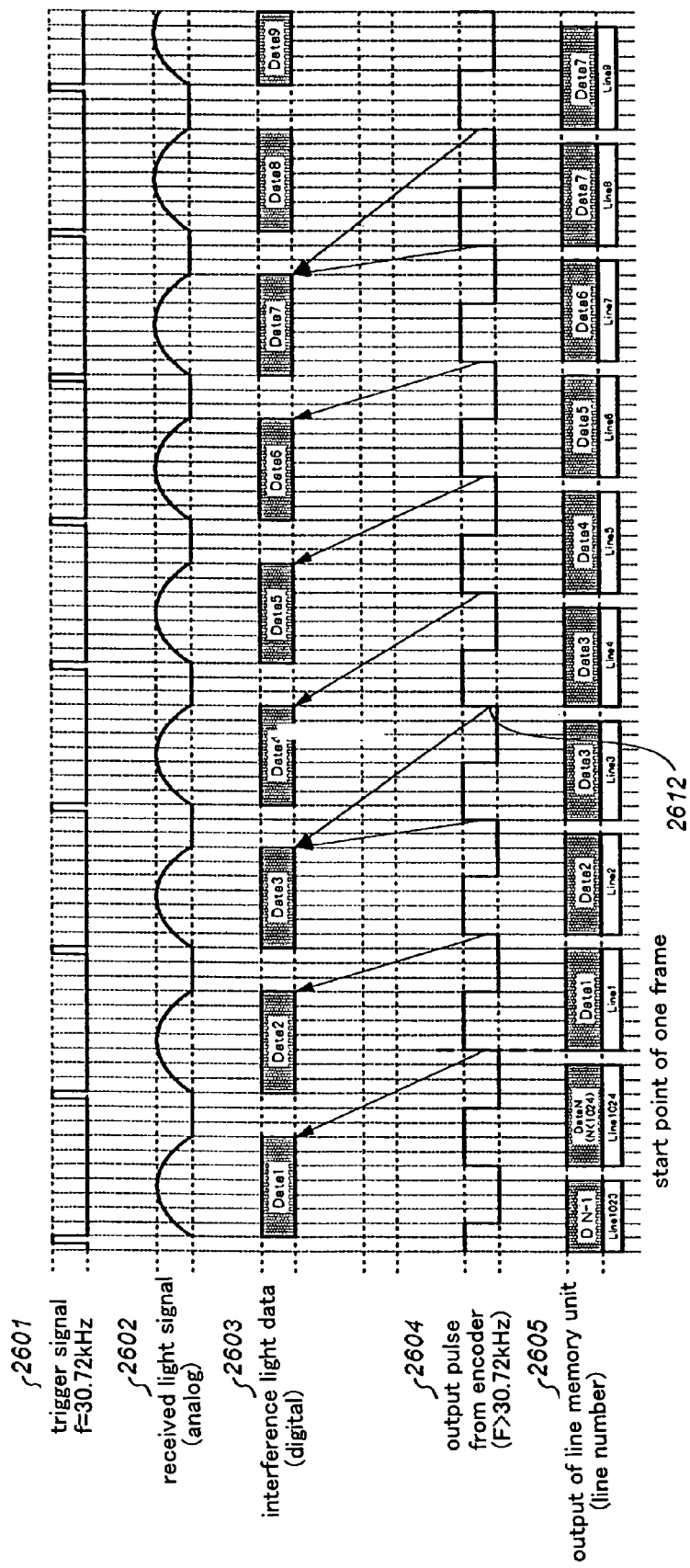
FIG. 26B is a timing chart illustrating when output pulses from an encoder and a timing of wavelength sweep of irradiation light are also out of synchronization.

FIG. 26B is a timing chart illustrating a situation in which the output pulses from the encoder 2206 and the timing of wavelength scanning cycle are out of synchronization. FIG. 26B shows that the output pulses from the encoder 2206 are advanced relative to the production timing of interference light data for an advance of the radial scan motor.

Specifically, FIG. 26B shows a state in which, because the output pulses from the encoder 2206 are advanced relative to the production timing of interference light data, the production of interference light data as Data 4 has not been completed at the time that Data 4 are supposed to be read and therefore the reading of Data 3 has been performed again.

In other words, at a time (2612) when an output pulse from the encoder 2206 has been received, the latest interference light data are determined to be Data 3 so that the reading of Data 3 is performed again.

As is evident from the above description, the OCT imaging system making use of a wavelength swept light source according to this embodiment makes it possible to perform appropriate reading of interference light data in accordance with the rotation cycle of the probe in radial scanning even when no synchronization is achieved between the rotation cycle of the probe in the radial scanning and the wavelength sweep cycle of light irradiated from the probe.

As a result, it is possible to reduce or eliminate difficulties encountered in other systems mentioned above in which a tomographic image may be displayed blurred in the circumferential direction or may be displayed while slowly turning.

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An image diagnostic system comprising:
    a probe positionable in a body cavity and configured to repeatedly transmit signals into a body cavity and receive reflected signals which are reflected by biotissue surrounding the body cavity;
    a control unit configured to produce data based on the reflected signals to construct a tomographic image of the body cavity and surrounding biotissue, the control unit comprising:
    a plural storage units configured to store the data in transmission/reception units;
    a writing control unit configured to control writing processing of the data in which the data is written in the storage units in accordance with a transmission/reception timing of the signals;
    a reading control unit configured to control reading processing of the data stored in the storage units in which the data stored in the storage units is read in accordance with a corresponding rotation angle of the probe;
    the writing control unit configured to control the writing processing to write the data in the storage unit corresponding to an oldest stored data;
    the reading control unit configured to control the reading processing to read the data in the storage unit corresponding to a newest stored data; and
    a display unit configured to display the tomographic image constructed by the control unit based on the data read by the reading control unit.

2. The image diagnostic system according to claim 1, wherein the probe comprises an ultrasonic transducer configured to transmit and receive ultrasounds.

3. The image diagnostic system according to claim 1, wherein the probe comprises an optical probe and an optical-probe connector adapted to be connected to a low-coherence light source configured to output the signal in the form of light, the control unit producing the data based on interference light between the light reflected in the body cavity and received through the optical probe and a reference light split from the light outputted from the low-coherence light source.

4. The image diagnostic system according to claim 3, wherein the light source is configured to output a wavelength-swept laser beam.

5. The image diagnostic system according to claim 1, wherein the writing control unit controls the writing processing to write the data to the storage unit corresponding to the oldest stored data and which is not being read by the reading control unit.

6. The image diagnostic system according to claim 1, wherein the reading control unit controls the reading processing to read the data from the storage unit corresponding to the newest stored data and which is not being written to by the writing control unit.

7. An image diagnostic apparatus for controlling a probe configured to be connected to the image diagnostic apparatus and which repeatedly transmits signals into a body cavity which are reflected by biotissue surrounding the body cavity to perform radial scanning within the body cavity, the image diagnostic apparatus comprising:
    a control unit configured to produce data based on the reflected signals and to construct a tomographic image of the body cavity and the biotissue surrounding the body cavity on a basis of the data; and
    a display unit configured to display the tomographic image, the control unit comprising:
    plural storage units configured to store the data in transmission/reception units;
    a writing control unit configured to control writing processing of the data in the storage units in accordance with a transmission/reception timing of the signals;
    a reading control unit configured to control reading processing of the data stored in the storage units in accordance with a corresponding rotation angle of the probe;
    the writing control unit configured to control the writing processing to write the data in the storage unit corresponding to an oldest stored data and which is not being subjected to reading processing;
    the reading control unit configured to control reading processing to read the data in the storage unit corresponding to a newest stored data and which is not being subjected to writing processing; and
    the tomographic image being constructed based on the data read by the reading control unit.

8. The image diagnostic apparatus according to claim 7, wherein the probe to which the image diagnostic apparatus is adapted to be connected comprises an ultrasonic transducer which transmits and receives ultrasounds, and the data is produced by the control unit based on ultrasound waves reflected in the body cavity and received through the probe.

9. The image diagnostic apparatus according to claim 7, wherein the probe to which the image diagnostic apparatus is adapted to be connected is connected to a light source capable of outputting light, with the probe being configured to transmit and receive the light, and the data are produced based on interference light between light reflected in the body cavity and received through the probe and a reference light split from the light outputted from the light source.

10. The image diagnostic apparatus according to claim 9, wherein the light source is configured to output a wavelength-swept laser beam.

11. A method for processing information in an image diagnostic system connected to a probe comprising:
   transmitting signals from the probe into a body cavity and receiving signals reflected from biotissue surrounding the body cavity;
   producing data based on the received reflected signals;
   performing writing processing of the data to store the data in individual storage units in accordance with a transmission/reception timing of the signals;
   performing reading processing of the data stored in the storage units to read the data in the storage units in accordance with a rotation angle of the probe;
   the writing processing being performed to write the data to the storage unit which is not being subjected to reading processing and corresponding to the data that is oldest;
   the reading processing being performed to read the data from the storage unit which is not being subjected to writing processing and corresponding to the data that is newest;
   constructing a tomographic image of the body cavity and surrounding biotissue based on the data that is read during reading processing; and
   displaying the tomographic image of the body cavity and surrounding biotissue.

12. A method for producing a tomographic image of a body cavity and surrounding biotissue comprising:
   positioning a probe in a body cavity;
   transmitting signals from the probe into the body cavity and receiving signals reflected from the biotissue surrounding the body cavity;
   producing data based on the received reflected signals;
   writing the data in individual storage units in accordance with a transmission/reception timing of the signals to store the data in the storage units, the data being written in the storage unit corresponding to the data that is oldest;
   reading the data stored in the storage units in accordance with a rotation angle of the probe, the data being read from the storage unit corresponding to the data that is newest and to which data is not being written;
   constructing a tomographic image of the body cavity and the surrounding biotissue based on the data that is read; and
   displaying the tomographic image of the body cavity and the surrounding biotissue.

13. The method according to claim 12, wherein the signals transmitted by the probe are ultrasound.

14. The method according to claim 12, wherein the signals transmitted by the probe are low-coherence light signals.

15. The method according to claim 14, wherein the low-coherence light signals are outputted by a light source, and the data are produced based on interference light between light reflected from the biotissue and a reference light split from the light outputted by the light source.

16. The method according to claim 12, wherein the transmitted signals are laser-beams outputted by a light source that outputs a wavelength-swept laser beam.

* * * * *